US007485655B2

(12) United States Patent
Linden et al.

(10) Patent No.: US 7,485,655 B2
(45) Date of Patent: Feb. 3, 2009

(54) 2-AMINOTHIAZOLE ALLOSTERIC ENHANCERS OF $A_1$ ADENOSINE RECEPTORS

(75) Inventors: Joel Linden, Charlottesville, VA (US); Timothy L. MacDonald, Charlottesville, VA (US); Lauren Murphree, Charlottesville, VA (US); Mahendra D. Chordia, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 403 days.

(21) Appl. No.: 10/499,291

(22) PCT Filed: Jan. 16, 2003

(86) PCT No.: PCT/US03/01396

§ 371 (c)(1),
(2), (4) Date: Jun. 18, 2004

(87) PCT Pub. No.: WO03/061655

PCT Pub. Date: Jul. 31, 2003

(65) Prior Publication Data

US 2005/0027125 A1 Feb. 3, 2005

Related U.S. Application Data

(60) Provisional application No. 60/349,191, filed on Jan. 16, 2002.

(51) Int. Cl.
*A61K 31/428* (2006.01)
*C07D 277/60* (2006.01)
(52) U.S. Cl. .......................... 514/366; 548/150; 514/366
(58) Field of Classification Search ................. 548/150; 514/366
See application file for complete search history.

(56) References Cited

U.S. PATENT DOCUMENTS

| 4,877,876 | A | * | 10/1989 | Tsuji et al. .................. 544/133 |
| 5,189,049 | A | | 2/1993 | Frehel et al. |
| 6,251,922 | B1 | * | 6/2001 | Jahne et al. .................. 514/338 |
| 6,476,059 | B1 | | 11/2002 | Jähne et al. |
| 6,713,638 | B2 | | 3/2004 | Linden et al. |

FOREIGN PATENT DOCUMENTS

| WO | WO 94/18212 | 8/1994 |
| WO | WO 99/42455 | 8/1999 |
| WO | WO 01/90092 A1 | 11/2001 |

OTHER PUBLICATIONS

Gupta, R et al, "Synthesis and antiinflammatory activity of some substituted 2-amino-8H-indeno[1,2-d]thiazoles," Indian J. Pharmaceutical Sciences, 1991, pp. 245-248.*

Esses-Reiter, K. et al, "Synthesis of C-nor-heterocyclic Steroid Analogs," J. Heterocyclic Chem., 1996, vol. 33, No. 3, pp. 879-884.*
International Search Report, corresponding to PCT/US03/01396, mailed on Jun. 5, 2003.
Gupta, R. et al., "Synthesis and Anti-inflammatory Activity of Some Substituted 2-amino-8H-indeno[1,2-d] thiazoles," vol. 117, 111516b, Sep. 14, 1992, p. 857.
Gupta, R. et al., "Synthesis and Anti-inflammatory Activity of Some Substituted 2-amino-8H-indeno[1,2-d] thiazoles," Indian Journal of Pharmaceutical Sciences, Jan. 30, 1991, pp. 245-248.
Chordia, M., et al., "2-Aminothiazoles: A New Class of Agonist Allosteric Enhancers of $A_1$ Adenosine Receptors," Bioorganic & Medicinal Chemistry Letters 12, Apr. 16, 2002, pp. 1563-1566.
Satish Kumar, et al., "Condensed Heterocyclics: Part XVII - Synthesis of Dihydrophenanthrocarbazole, Dihydrophenanthrothiarole, dihydrophenanthroisoxazole 7 Dihydrophenanthropyrazole," Indian J. Chem., vol. 21B, Jun. 1982, pp. 591-593.
European Search Report issued Jun. 24, 2008, 9 pages.
A.V. Naidu, et al., "Synthesis and Biological Activities of Substituted-1-Tetralone Derivatives: Part II," Asian Journal of Chemistry, vol. 12, No. 3 (2000), pp. 687-692.
K. Ramalingam, et al., "Synthesis and Antimicrobial Activity of Azasteroid-Type Compounds and Related Systems. Effect of Hydrophilic and Lipophilic Groups on Activity," Journal of Medicinal Chemistry, 1977, vol. 20., Nov. 5, pp. 664-669.
Klara Esses-Reiter, et al., "Synthesis of C-nor-Heterocyclic Steroid Analogues," TIB Hannover, May-Jun. 1996, pp. 879-884.
Mitsuru Ohkubo, et al., "Studies on Cerebral Protective Agents. VIII. synthesis of 2-Aminothiazoles and 2-Thiazolecarboxamides with Anti-anoxic Activity," Chem. Pharm. Bull. 43(9) 1497-1504 (Sep. 1995).
K. Darrell Berlin, et al., "Novel 2-Amino-4-Aryl-Substituted-and 2-Amino-4, 5-Disubstituted-Thiazoles," Department of Chemistry, Oklahoma State Univ., Feb. 20, 1991, pp. 29-33.
V.F. Kucherov, "Amino Derivatives of the Heterocyclic Series. III. Polycyclic Analogs of Aminothiazole," Zhurnal Obshschei Khimi 20, 1950, pp. 1658-1661.
Rebecca Brown, et al., "Biological Activity and Active Groups of Novel Pyrazoles, Thiosemicarbazones, and Substituted Thiazoles," Proc. Oklahoma Acad. Sci., vol. 56, Jan. 1, 1976, pp. 15-17.
Abstracts From Purines 2001, p. 558.
Lingaiah Nagarapu, et al., "Synthesis of Phenylimidazo Thiazolo benzocycloheptene Derivates as Potential Antiinflammatory Agent - IV," Indiana Institute of Chemical Technology, Hyderabad-500 007, India, vol. 7, No. 6, pp. 535-540.

* cited by examiner

*Primary Examiner*—Kamal A Saeed
*Assistant Examiner*—Janet L Coppins
(74) *Attorney, Agent, or Firm*—J. Clinton Wimbish; Kilpatrick Stockton, LLP

(57) ABSTRACT

The present invention relates generally to a class of 2-aminothiazole derivatives which have recently been identified as allosteric enhancers of the $A_1$ adenosine receptor. These compounds, and therapeutic compositions containing them, are useful for treating conditions in which activation of the $A_1$ adenosine receptor would be beneficial, for example, those conditions in which stimulation of angiogenesis would improve blood flow to ischemic tissues.

9 Claims, 17 Drawing Sheets

Formation of Neutral amino thiazoles n=1, 2 or 3

Synthesis of 8H-Indeno[1,2-d]thiazol-2-ylammonium iodide derivatives
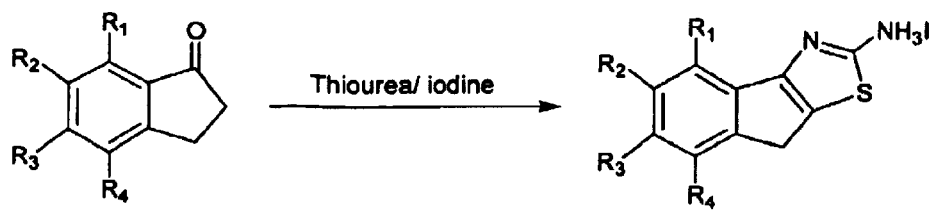
R₁,R₂,R₃ = OMe
R₂,R₃,R₄ = OMe
R₄=OAc
R₃=OH,R=alkyl,allyl etc.
R₄=OH, R₃=alkyl, allyl etc.
Synthesis of 5-Methyl-4,5-dihydro-naphtho[1,2-d]thiazol-2-ylammonium iodide
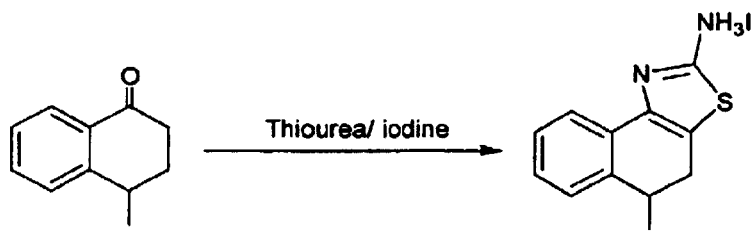
Fig. 7

**Synthesis of 6-Aryl-*8H*-indeno[1,2-d]-thiazol-2-ylamine hydroiodide** a. Pd(OAc)$_2$, K$_2$CO$_3$, Bu$_4$NBr
H$_2$O, 70-80 °C
b. I$_2$, Thiourea, DMF or EtOH
heating R = mono, di, tri, tetra or penta substituted aromatic derivatives
R = alkyl, aryl, amino, hydroxy, alkylhydroxy, alkoxy, amido, aryloxy, acetoxy, bromo, fluoro, nitro or combination of thereof etc.

**Synthesis of 5-Aryl-6-methoxy-*8H*-indeno[1,2-*d*]-thiazol-2-ylamine hydroiodide**

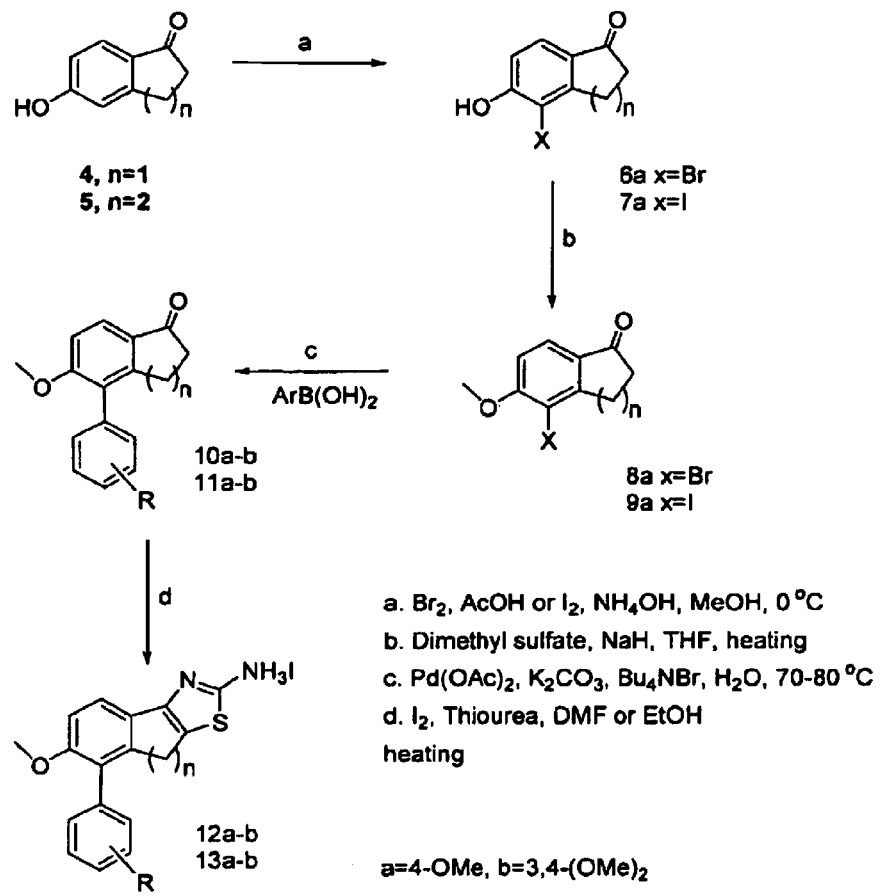

a. $Br_2$, AcOH or $I_2$, $NH_4OH$, MeOH, 0 °C
b. Dimethyl sulfate, NaH, THF, heating
c. $Pd(OAc)_2$, $K_2CO_3$, $Bu_4NBr$, $H_2O$, 70-80 °C
d. $I_2$, Thiourea, DMF or EtOH heating a=4-OMe, b=3,4-$(OMe)_2$ R = mono, di, tri, tetra or penta substituted aromatic derivatives
R = alkyl, aryl, amino, hydroxy, alkylhydroxy, alkoxy, amido, aryloxy, acetoxy, bromo, fluoro, nitro or combination of thereof etc.

Fig. 10

**Synthesis of 6-Methoxy-7-aryl-*8H*-indeno[1,2-d]-thiazol-2-ylamine hydroiodide**

R = mono, di, tri, tetra or penta substituted aromatic derivatives
R = alkyl, aryl, amino, hydroxy, alkylhydroxy, alkoxy, amido, aryloxy, acetoxy, bromo, fluoro, nitro or combination of thereof etc.

Detailed Scheme for the Synthesis of N-(2-Amino-5-Aryl-8H- indeno [1,2-d] thiazol-6yl) -acetamide Derivatives

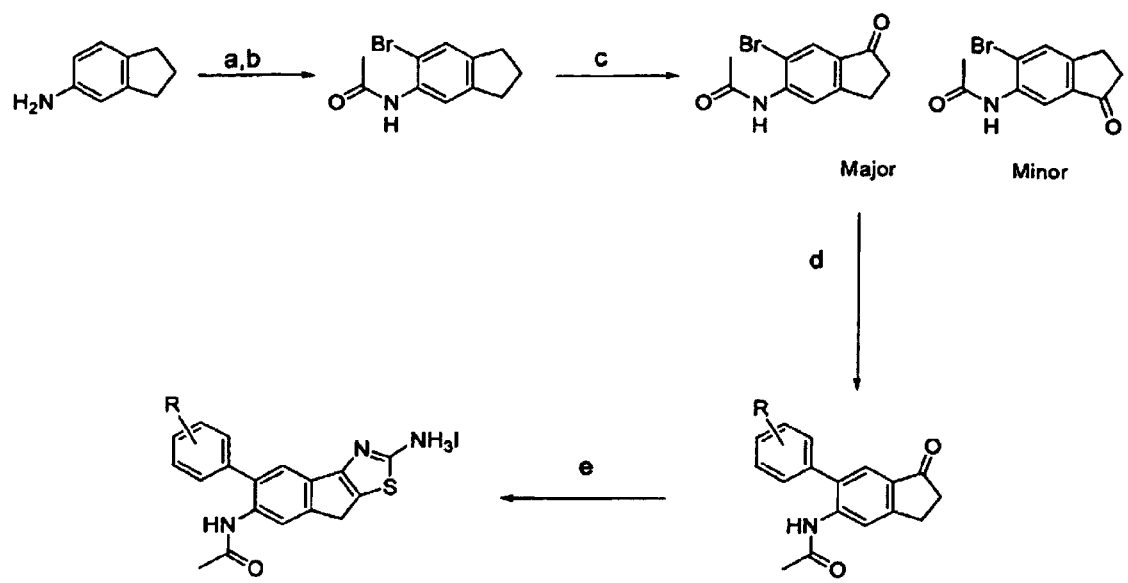

a. $Ac_2O$, Pyridine, RT; b. $Br_2$/AcOH 0°-RT; c. $CrO_3$/AcOH, d. $Pd(OAc)_2$, $K_2CO_3$, $Bu_4NBr$, $H_2O$, heating; e. Thiourea, $I_2$, EtOH, heating R = mono, di, tri, tetra or penta substituted aromatic derivatives
R = alkyl, aryl, amino, hydroxy, alkylhydroxy, alkoxy, amido, aryloxy, acetoxy, bromo, fluoro, nitro or combination of thereof etc.

Fig. 13

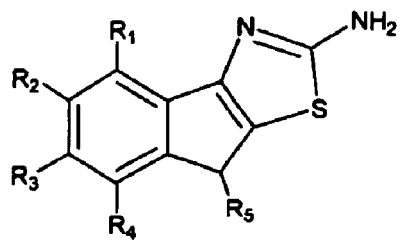
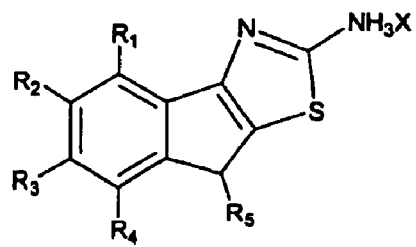
X= Cl, Br, I or CH₃COO⁻
CF₃COO⁻ etc.
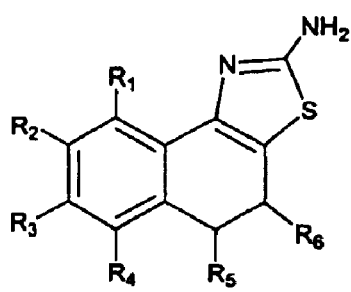
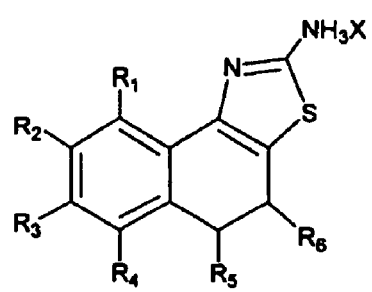
X= Cl, Br, I or CH₃COO⁻
CF₃COO⁻ etc.
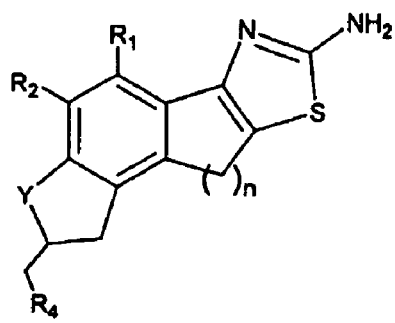
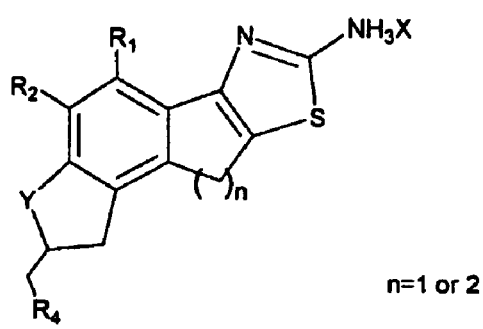
n=1 or 2
X= Cl, Br, I or CH₃COO⁻
CF₃COO⁻ etc.
Y=O
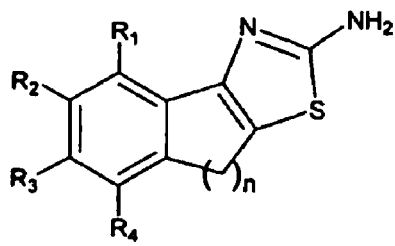
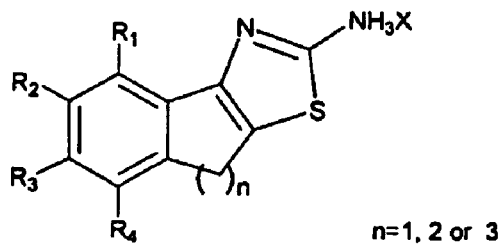
n=1, 2 or 3
Fig. 14

2-AMINOTHIAZOLE ALLOSTERIC ENHANCERS OF $A_1$ ADENOSINE RECEPTORS

CROSS REFERENCE TO RELATED APPLICATION

This application claims the benefit of U.S. Provisional Application No. 60/349,191 filed in the United States Patent Office on Jan. 16, 2002.

BACKGROUND OF THE INVENTION

FIELD OF THE INVENTION

Adenosine is a nucleoside present in all cell types of the body. It is endogenously formed and released into the extracellular space under physiological and pathophysiological conditions characterized by an increased oxygen demand/supply ratio. Accordingly, adenosine production is accelerated in conditions with increased high energy phosphate degradation. The biological actions of adenosine are mediated through specific cell surface G protein-coupled receptors of four known subtypes, $A_1$, $A_{2A}$, $A_{2B}$ and $A_3$.

The present invention relates to a new class of compounds known as allosteric modulators, or allosteric enhancers, of the $A_1$ adenosine receptors. These compounds binding to an allosteric site on the receptor that is distinct from the orthosteric site occupied by adenosine. Previously known $A_1$ enhancers are derivatives of 2-amino-3-benzoylthiophene, such as those first described by Bruns et al., *Allosteric enhancement of adenosine $A_1$ receptor binding and function by 2-amino-3-benzoylthiophenes*, Mol. Pharmacol., 38, 939-949 (1990). By themselves, allosteric enhancers are not full agonists at the $A_1$ adenosine receptor, i.e. they produce only partial receptor activations. At low concentrations, they enhance the effect of orthosteric $A_1$ receptor agonists which are generally adenosine derivatives. At higher concentrations, some allosteric enhancers can act as antagonists of the $A_1$ receptor, resulting in a limited concentration range in which these compounds can enhance the effects of agonists. The receptor antagonist activity of the compounds is not well correlated with the enhancer activity, indicating that the antagonist and enhancer activities are not interdependent.

Mechanistically, the benzoylthiophene allosteric enhancers appear to enhance $A_1$ adenosine receptor function by stabilizing the high affinity state of the receptor-G-protein complex. This property is manifested as an increase in high affinity binding in radioligand binding reactions where an orthosteric agonist radioligand is used to label the $A_1$ adenosine receptor. An enhancer that increases agonist binding can do so by either accelerating the association of agonist and receptor, or by retarding the dissociation of the receptor-ligand complex, especially to the high affinity complex that also contains an associated G protein. Kinetic studies have shown the benzoylthiophenes to retard the dissociation of the receptor-ligand complex. In contrast, conventional orthosteric agonists and antagonists will each compete with the radioligand for the binding site, but do not change the dissociation kinetics of the radioligand from the receptor. Since the benzoylthiophenes only selectively retard the dissociation of the receptor-ligand complex when an agonist radioligand is used, they must bind to a site different from the agonist recognition site. This putative site is termed the allosteric site, and presumably, compounds that bind to this site and enhance the agonist effect are termed "allosteric enhancers."

Allosteric enhances of the $A_1$ adenosine receptor are therapeutically significant, as adenosine receptor $A_1$ agonists in general promote angiogenesis (blood vessel formation), and selective $A_1$ allosteric enhancers are expected to selectively stimulate angiogenesis in ischemic tissues that produce high levels of adenosine, as opposed to tissue which has adequate blood flow in which the adenosine concentation is low.

BRIEF SUMMARY OF THE INVENTION

The present invention relates generally to a class of 2-aminothiazole derivatives which have recently been identified as allosteric enhancers of the $A_1$ adenosine receptor. These compounds, and therapeutic compositions containing them, are useful for treating conditions in which activation of the $A_1$ adenosine receptor would be beneficial; for example, those conditions in which stimulation of angiogenesis would improve blood flow to ischemic tissues.

Accordingly, the present invention provides a class of novel compounds which are 2-aminothiazole derivatives and which act as allosteric enhancers of the $A_1$ adenosine receptor in mammalian, including human, subjects.

The invention also includes use of such novel compounds and also previously known 2-aminothiazole derivatives, as allosteric enhancers of the $A_1$ adenosine receptor in mammalian, including human, subjects.

The invention further includes a method of promoting angiogenesis in a mammalian subject, such as a human, via the administration of a 2-aminothiazole compound, which acts as an allosteric enhancer of the $A_1$ adenosine receptor.

The invention additionally includes the use of such 2-aminothiazole compounds in the manufacture of medicaments for the treatment of a condition or symptom in a mammalian subject, such as a human, which can be treated by angiogenesis promotion.

Additionally, the invention provides a therapeutic method for preventing or treating a pathological condition or symptom in a mammal subject, such as a human, wherein increased angiogenesis is desired, comprising administering to a mammal in need of such therapy an effective amount of a 2-aminothiazole $A_1$ adenosine receptor allosteric enhancer, either alone or in combination with a selective $A_1$ adenosine receptor agonist.

The invention also includes the use of a combination of a 2-aminothiazole $A_1$ adenosine receptor allosteric enhancer with a selective $A_1$ adenosine receptor agonist for synergistic stimulation of angiogenesis in a mammalian subject, such as a human.

Inhibitors of the $A_1$ adenosine receptor are also potential drug candidates for conditions in which inhibiting angiogenesis is desirable. For example, in various cancers, angiogenesis is required for tumor growth. Tumors become hypoxic while growing and induce angiogenesis to supply additional oxygen. Inhibitors of $A_{2B}$ adenosine receptors are know to inhibit angiogienesis due to effects of endothelial cells. However, our data indicated for the first time that blockers of $A_1$ receptors also may be effective as inhibitors of angiogensis. In response to the adenosine released during the hypoxic stage, antagonists would bind to $A_1$ receptors and inhibit their function, thus arresting the signaling cascade that would lead to blood vessel formation. Additionally, unwanted blood vessel formation in the eye leads to various retinopathies. Infants are particularly prone to over vascularization in the eye following hypobaric oxygen treatment, which can lead to blindness if left untreated.

BRIEF DESCRIPTION OF THE DRAWING FIGURES

Various other objects, features and attendant advantages of the present invention will become more fully appreciated as the same becomes better understood when considered in conjunction with the accompanying drawings.

FIG. 1-FIG. 13 illustrates various reaction schemes for producing a variety of 2-aminothiazole derivatives of the present invention.

FIG. 14-FIG. 17 illustrates representative examples of various 2-aminothiazole derivatives.

DETAILED DESCRIPTION OF THE INVENTION

Figure 1:
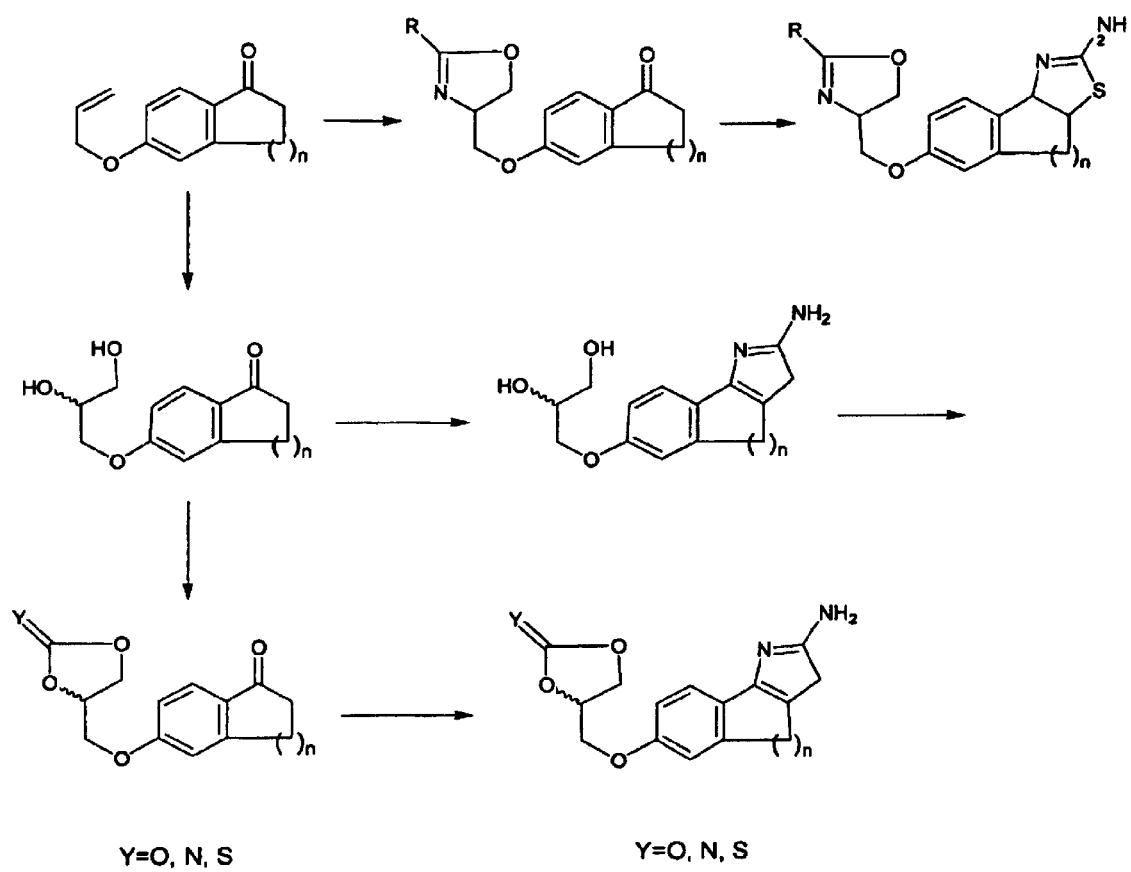
Figure 2:
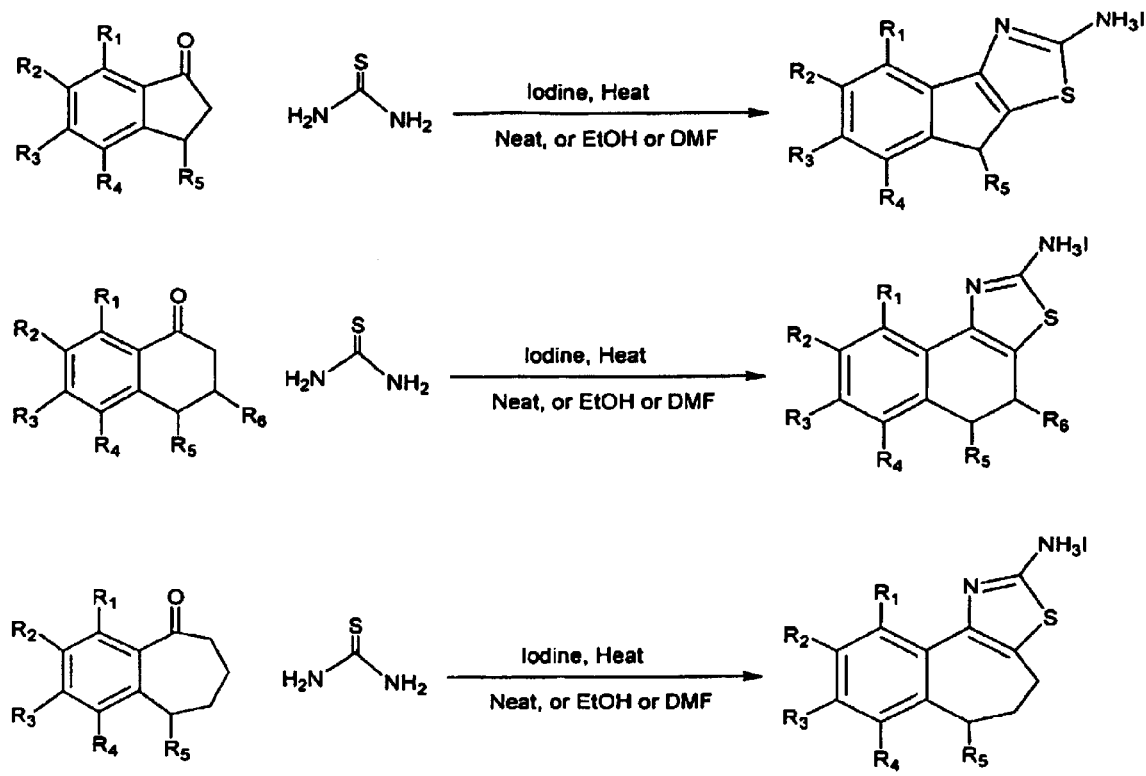
Figure 3:
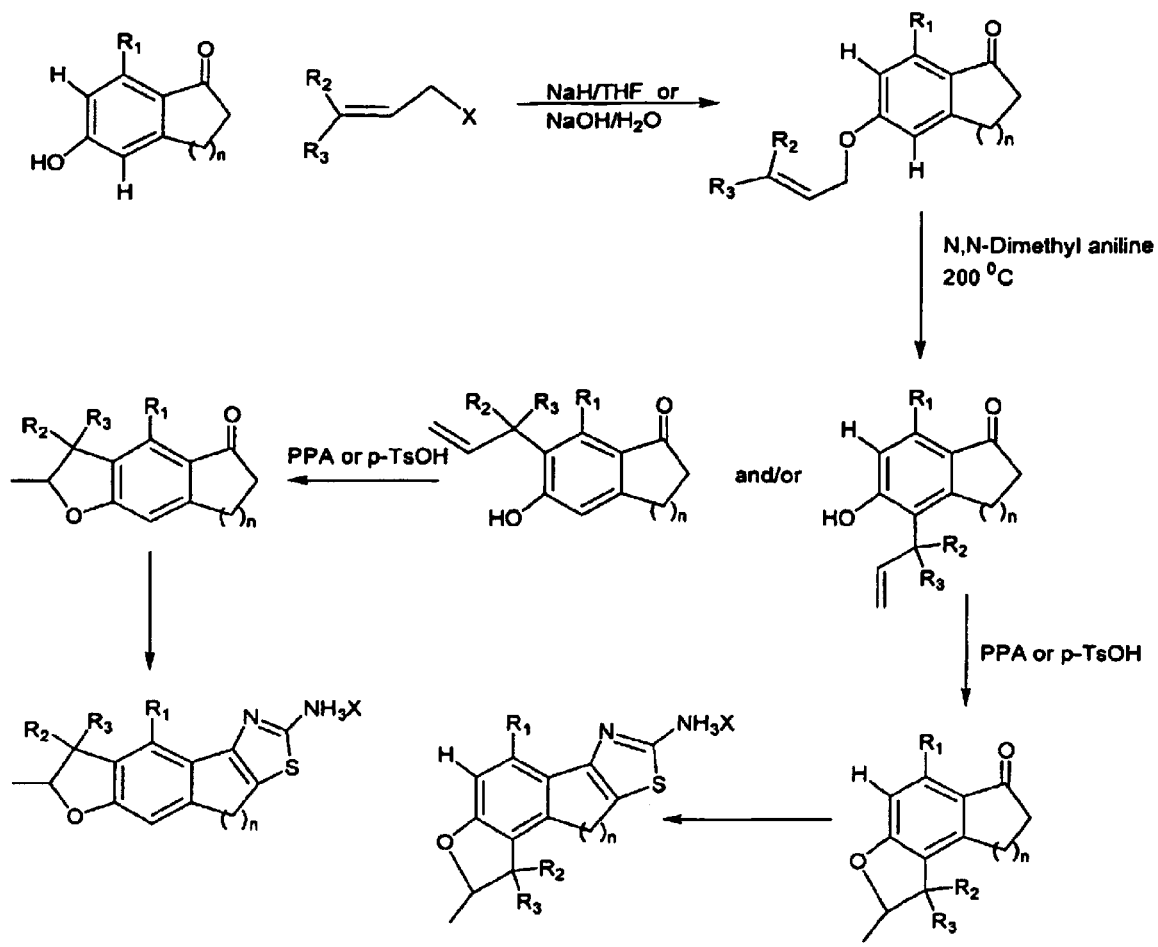
Figure 4:
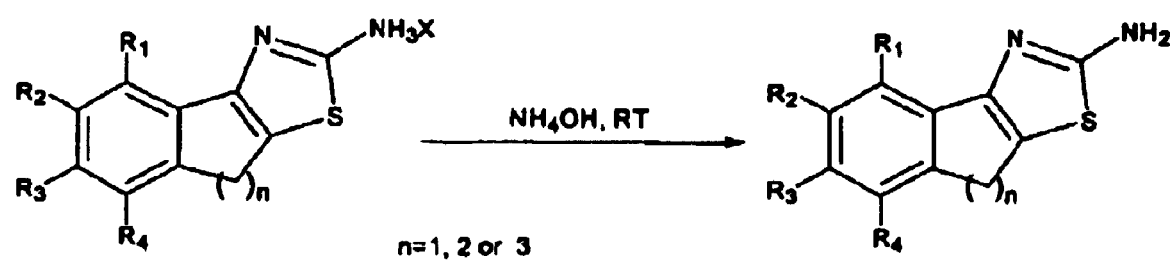
Figure 5:
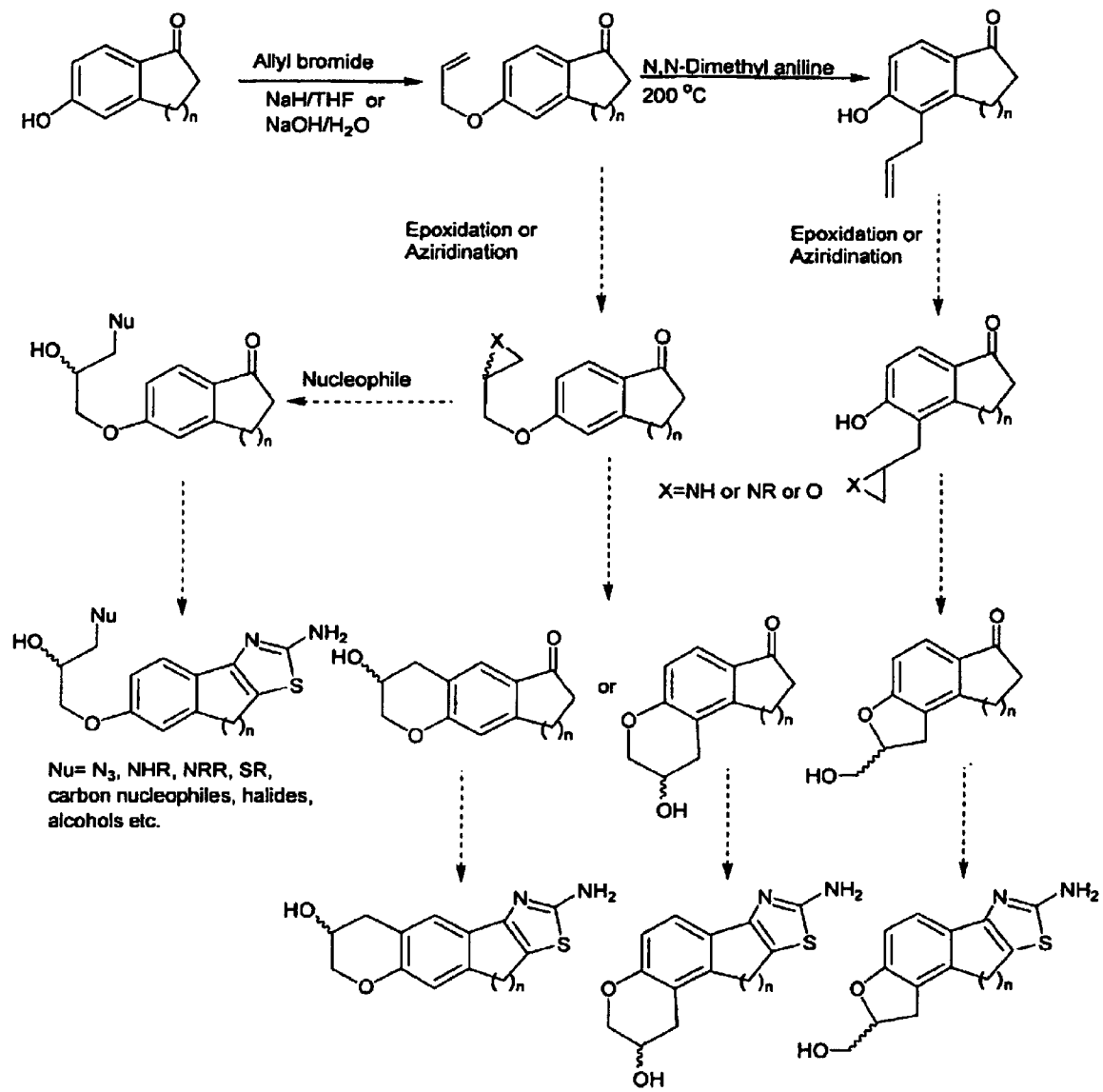
Figure 6:
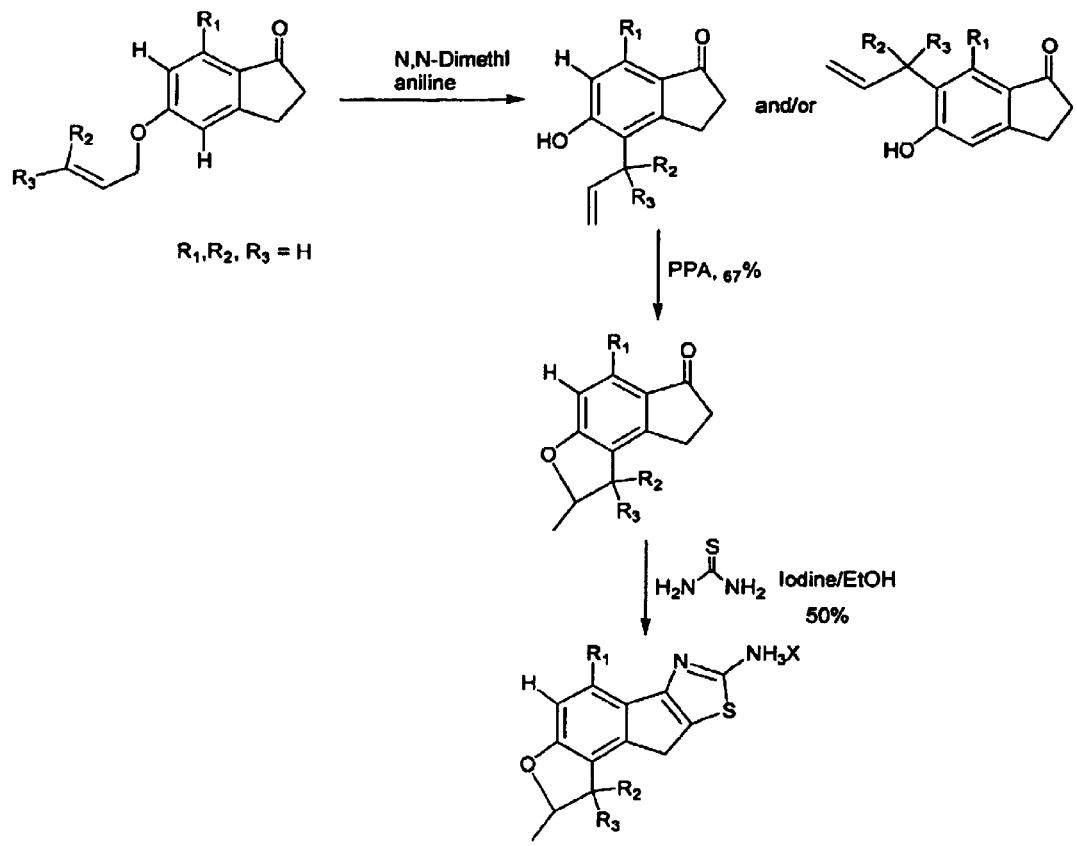

Angiogenesis is the process whereby new vessels are formed from previously formed ones and is a complex process involving a coordinated interaction between numerous cell types. The critical cells are the endothelial cells that contain all of the genetic information necessary to form primitive tubes and branches. Other cells, such as smooth muscle cells, mast cells, and macrophages release important modulators of angiogenesis. Hypoxia, decreased blood flow, and released angiogenic substances such as vascular endothelial growth factor (VEGF) can trigger angiogenesis. Angiogenesis is initiated by a breakdown in the extracellular matrix followed by proliferation and migration of endothelial cells into the tissue. Initially, the endothelial cells form cords, and subsequently large vacuoles form in the cells, leading to the formation of tubes. These endothelial tubes have a lumen, but are abnormally permeable and leaky until pericytes are recruited to reinforce the new vessels. Several growth factors, most notably VEGF, bFGF and angiopoetin-1, have been demonstrated to promote angiogenesis. VEGF, a specific mitogen for endothelial cells, can independently stimulate new vessel growth. However, over expression of VEGF in developing avian embryos results in large diameter vessels that are leaky, leading to tissue edema. The coordinated effects of several growth factors may be necessary in order to stimulate development of normal new vasculature. Hence, finding ways to use upstream modulators in a tissue-specific way is expected to provide a therapeutic advantage over the application of individual angiogenic growth factors.

There are widespread clinical applications for the stimulation of the angiogenic process, for example, in cardiovascular medicine and ophthalmology. Stimulating new vasculature in ischemic tissues, especially heart and limbs, could have a major impact on morbidity and mortality from atherosclerotic disease and is currently an active clinical endeavor. Trials in humans have shown the usefulness of VEGF in stimulating collateralization to ischemic lower extremities, resulting in improved ulcer healing and decreased limb loss. There are also ongoing clinical trials using VEGF infusions in patients with intractable, inoperable angina.

VEGF is a direct, or primary, angiogenic factor, meaning that it is able independently to induce angiogenesis in endothelial cells in vitro or in vivo. Secondary, or indirect, angiogenic factors work by causing cells to release primary factors. There is apprehension among scientists and clinicians about using primary factors clinically for fear that there will be pathologic angiogenesis in other tissues. Thus a limitation of using adenosine or other promoters of angiogenesis is the potential for neovascularization in healthy as well as diseased tissues. Inhibition of angiogenesis to curtail tumor growth is as important a quest in oncology as stimulating it is in cardiovascular medicine, so the prospect of abnormal vessel stimulation is a significant concern. Additionally, while VEGF is sufficient to stimulate the formation of new blood vessels, there is evidence that the growth of normal healthy vessels may require a coordinated action among several different growth factors. Hence, activation of upstream secondary-angiogenic stimuli may produce a more regulated and normal vascular response. Additionally, the ability to target angiogenic stimulation to specific tissues would diminish the risk of undesirable systemic angiogenesis.

Adenosine has been shown to trigger angiogenesis in animal models and endothelial cell proliferation in cultured cells. Adenosine as a modulator of angiogenesis can be studied using the chicken chorioallantoic membrane (CAM) model. In addition, hypoxia initiates proliferation of cultured endothelial cells, a response that can be blocked by nonselective adenosine receptor antagonists. Hypoxia has long been considered a driving force for new blood vessel formation. Increased vascular density is seen in humans at high altitudes, in chronically stimulated skeletal muscle, and in rapidly growing tumors. In the CAM model, lowering oxygen concentration stimulates neovascularization. Adenosine is a logical modulator for the hypoxic stimulation of angiogenesis. It is a metabolite of ATP breakdown released from all ischemic or hypoxic tissues where it acts as a "retaliatory metabolite" to released from all ischemic or hypoxic tissues where it acts as a "retaliatory metabolite" to Adenosine acts via cell surface G protein coupled receptors of four known subtypes, $A_1$, $A_{2A}$, $A_{2B}$ and $A_3$. $A_1$ and $A_3$ receptors are the most similar in amino acid sequence and pharmacology. The $A_1$ and $A_3$ receptors couple to G proteins from the Gi/Go family that are pertussis toxin sensitive and inhibit adenylyl cyclase. Stimulation of $A_1$ and $A_3$ receptors can also activate phospholipase C, presumably via G protein βγ subunits. $A_{2A}$ and $A_{2B}$ receptors couple to Gs and stimulate adenylyl cyclase, but the $A_{2B}$ receptor can also couple to Gq, which is insensitive to pertussis toxin. In the heart, $A_1$ receptors have negative chronotropic, dromotropic and inotropic effects. The $A_1$ receptor, and perhaps the $A_3$, is also involved in the preconditioning phenomenon which protects ischemic myocardium. $A_{2A}$ receptors are expressed on coronary arteries and activation results in coronary vasodilation. $A_{2A}$ receptors are also found on leukocytes where they act to attenuate the inflammatory response and hence may decrease reperfusion injury. Accordingly, adenosine acts in a number of ways to protect ischemic tissues; it decreases metabolism, increases blood flow, and attenuates inflammatory injury. Adenosine activates $A_{2B}$ receptors on cultured endothelial cells to trigger VEGF release and endothelial mitogenesis. Adenosine also appears to stimulate angiogenesis, but to date no attempt has been made to define the adenosine receptor subtypes involved in the CAM model. Additionally, until the present invention it had not been shown that adenosine stimulates angiogenesis in adult mammalian models. The new development of more selective adenosine receptor ligands and cloning of the chicken $A_1$, $A_{2A}$, and $A_3$ receptors has enabled us to identify adenosine receptor subtypes participating in the CAM angiogenic response to adenosine.

Previous studies suggest that adenosine is released from hypoxic or ischemic tissue and that adenosine stimulates angiogenesis. Possible mechanisms include increased flow, stimulation of vascular cell proliferation and migration, or stimulation of angiogenic growth factor secretion. Some of the results obtained in previous studies on adenosine effects in vivo and in vitro have suggested that activation of adenosine $A_2$ receptors ($A_{2A}$ or $A_{2B}$) is responsible for the ability of adenosine to stimulate angiogenesis. The activation of $A_{2B}$ receptors on cultured endothelial cells has been shown to stimulate VEGF release. Most previous studies show a role for the $A_{2A}$ or $A_{2B}$ receptors, but little or no role for $A_1$ adenosine receptor activation in stimulating angiogenesis. The present invention is based on data showing that the $A_1$ receptor is more important than has been previously thought. The compounds of the present invention are clinically significant because they are allosteric enhancers that selectively increase the functional effects of endogenous adenosine or adenosine agonists at the $A_1$ receptor. Allosteric enhancers of $A_1$ adenosine receptors are expected to selectively stimulate angiogenesis in ischemic tissue and not in tissue that has adequate blood flow. This site-specificity represents a major advantage over other angiogenic agents that are not selective for ischemic tissue.

Adenosine receptors are activated by modified analogues of adenosine and inhibited by xanthines, such as caffeine and other alkylxanthines. Xanthine antagonists of adenosine receptors have been shown to block the effects of hypoxia to stimulate endothelial cell proliferation. Recently non-xanthine antagonists have been described as well. The pharmacology of a given adenosine receptor subtype can vary widely among species. This is particularly true for the $A_1$ and $A_3$ receptors. The $A_1$ and $A_3$ receptors differ most among species in the binding of xanthine antagonists. $A_{2A}$ receptors show less variation in binding among species. The $A_{2B}$ receptor is a low affinity receptor for which there were no selective ligands until recently. While not extensively characterized, the recombinant chicken $A_1$ receptor shows a rank order potency for adenosine agonist ligands that is similar to that of rat and human $A_1$ receptors.

Cyclopentyladenosine (CPA) has long been known as a highly selective $A_1$ agonist, while the newly described non-xanthine antagonist WRC-0571 offers increased $A_1$ selectivity, especially between $A_1$ and $A_3$ receptors. CGS21680 is a potent and highly selective $A_{2A}$ agonist for all species studied to date; however, until recently, there were no stable, highly selective $A_{2A}$ antagonists. Now, several new highly selective $A_{2A}$ antagonist compounds are available, including ZM-241385, which block $A_{2A}$ receptors much more potently than $A_1$ receptors. The first $A_3$ receptor selective ligands have been recently described, and include the agonist $N^6$-iodobenzyl-5'-N-methyl-carboxamidoadenosine (IB-MECA) and the antagonist MRS 1191. MRS1191 offers >1300-fold selectivity for the human $A_3$ over the $A_1$ receptor. Table 1 shows the ligands we have used to characterize the angiogenic response seen in the CAM.

TABLE 1

|  | $A_1$ | $A_{2A}$ | $A_{2B}$ | $A_3$ |
|---|---|---|---|---|
| Agonist | CPA | CGS21680 | NECA | IB-MECA |
| Antagonist | WRC-0571 | ZM-241385 | Enprofylline | MRS 1191 |

As discussed above, endothelial cells have all four subtypes of adenosine receptors, $A_1$, $A_{2A}$, $A_{2B}$ and $A_3$. Microvascular endothelial cells in culture proliferate and migrate in response to adenosine, but there is controversy surrounding which receptor subtype is responsible, especially for the proliferative response. The concentrations of agonists used in several of the previous investigations were too high to be subtype selective. Reports differ with respect to whether an increase in cAMP inhibits or stimulates a proliferative endothelial cell response. Several investigators report that the proliferative response is a result of $A_2$ receptor stimulation, however, it is pertussis sensitive, suggesting that it may result from $A_1$ or $A_3$ stimulation. Nitric oxide stimulates proliferation and migration of endothelial cells and adenosine upregulates endothelial cell nitric oxide synthase via an $A_2$ mechanism. Adenosine also upregulates VEGF mRNA and protein expression in several cell types, some via $A_2$ receptors, probably $A_{2A}$, and some via $A_1$. Finally, adenosine agonists stimulate proliferation of smooth muscle cells associated with a decrease in cAMP, suggesting that it is mediated by the $A_1$ or $A_3$ receptor subtype.

Several different adenosine receptor subtypes may be involved in coordinating angiogenesis, but our data obtained from the CAM assay during development of the current invention unexpectedly point to a major role for the adenosine $A_1$ receptor. We have discovered that stimulation of adenosine $A_1$ receptors with either selective $A_1$ agonists or allosteric enhancers selective for $A_1$ receptors elicits an angiogenic response in the CAM model.

Allosteric enhancers of receptors are defined as compounds that potentiate responses to agonists and bind to an allosteric site distinct from the binding site of the endogenous ligand. For example, benzodiazepines are allosteric enhancers of $GABA_A$ receptors. There are a number of other receptors for which allosteric enhancers or inhibitors have been described, including the muscarinic receptors and atrial natriuretic receptors. Allosteric enhancers of adenosine $A_1$ receptors are compounds that have little effect by themselves, but enhance the adenosine $A_1$ receptor effects of endogenous adenosine in ischemic tissues.

PD 81,723 (PD) and the related compound C17 are members of a family of aminothiophene compounds that were the first described allosteric enhancers of adenosine $A_1$ receptors. These compounds increase binding of [$^3$H]$N^6$-cyclohexyladenosine (CHA) to adenosine $A_1$ receptors and cause a functional enhancement of the effects of adenosine $A_1$ receptor activation in various tissues. These aminothiophene compounds are selective for adenosine $A_1$ receptors, having no effects on receptors of other classes or on other adenosine receptor subtypes. PD has shown enhancement at $A_1$ receptors from all species tested to date. In the absence of adenosine or $A_1$-selective agonists, the enhancer molecules alone act as very weak antagonists for adenosine receptors. The ability of the aminothiophene allosteric enhancers PD 81,723 and C17 to promote angiogenesis in two animal model systems, a chicken chorioallantoic membrane model and a rat mesenteric model, has been demonstrated. This indicates that the $A_1$ receptor plays an important, but previously unrecognized, role in angiogenesis. Accordingly, selective adenosine $A_1$ receptor allosteric enhancers would theoretically work best in hypoxic tissues with high endogenous levels of adenosine, sparing other tissues from angiogenic effects where they are not needed.

Promoting angiogenesis is beneficial for revascularization of ischemic tissues in conditions such as stroke, heart disease, and peripheral vascular disease. Methods for treating stroke, heart disease, and peripheral vascular disease can thus effectively employ the administration of a compound, which promotes angiogenesis. The administration of such a compound can also be an effective method for treating cardiac arrhythmias, seizures and chronic pain, as well as, for inducing sleep. The aforementioned ability of compounds which are selective adenosine $A_1$ receptor allosteric enhancers to promote angiogenesis in two animal model systems, the chicken chorioallantoic membrane model and the rat mesenteric model, indicates that administration of such allosteric enhancer compounds enhance the ability of adenosine to promote angiogenesis, and may thus be advantageously employed therapeutically in patients with ischemic diseases to selectively stimulate angiogenesis in diseased tissues. Ischemic diseases include, but are not limited to angina, myocardial infarction, stroke, perpheral vascular disease and infertility.

The present invention is directed to the preparation and use of a class of 2-aminothiazole derivatives, which are selective allosteric enhancers for the $A_1$ adenosine receptor. These compounds have the general formula (I):

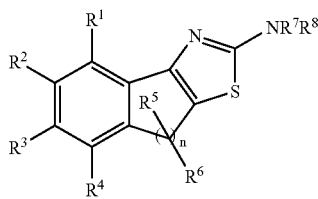

where in n is an integer from 1 to 3;

$R^1$, $R^2$, $R^3$, $R^4$ and $R^6$ are each independently hydrogen, halo, alkyl, alkoxy, alkoxyalkyl, alkylamino, haloalkoxy, cycloalkyl, cycloalkoxy, cycloalkylamino, alkenyl, alkenoxy, alkenylamino, alkynyl, alkynoxy, alkynylamino, aryl, arylalkyl, heteroaryl, heteroarylalkyl, nitro, thio, alkylthio, alkylthioalkyl, alkylsulfoxy, alkylsufonyl or ketoalkyl, with the aryl moiety in said aryl and arylalkyl groups, and the heteroaryl moiety in said heteroaryl and heteroarylalkyl groups, being optionally substituted with one or more substituents selected from halo, cyano, alkyl, aryl, heteroaryl, alkenyl, alkoxy, alkenyloxy, alkoxyalkyl, halosubstituted alkyl, halosubstituted alkoxy, alkoxycarbonyl, aminocarbonyl, nitro, thio, alkylthio and alkylthioalkyl, and wherein $R^1$ and $R^2$, $R^2$ and $R^3$, or $R^3$ and $R^4$, together with the carbon atoms to which they are attached, may optionally form a 5, 6 or 7-membered ring containing zero to two heteroatoms selected from N, O and S and which may be optionally substituted with one or more substituents selected from halo, cyano, alkyl, alkenyl, alkoxy, alkenyloxy, alkoxyalkyl, halosubstituted alkyl, halosubstituted alkoxy, alkoxycarbonyl, aminocarbonyl, nitro, thin, alkylthio and alkylthioalkyl;

$R^5$ is hydrogen, halo or lower alkyl; and $R^7$ and $R^8$ are each independently hydrogen, alkyl or arylalkyl;

or a pharmaceutically acceptable salt thereof.

As used herein, the tern "halo" means fluoro, chloro, bromo or iodo.

The term "alkyl" is used herein to mean straight or branched hydrocarbon chain radicals including, but not limited to, methyl, ethyl, n-propyl, isopropyl, n-butyl, and the like.

The term lower alkyl means an alkyl group having from one to about four carbon atoms.

The term "alkoxy" is used herein to mean —O-alkyl, including, but not limited to, methoxy, ethoxy, propoxy, isopropoxy, n-butoxy and the like.

The term "alkylthio" is used herein to mean —S-alkyl, including, but not limited to, methylthio, ethylthio, n-propylthio, isopropylthio, n-butylthio and the like.

The term "alkenyl" is used herein to mean straight or branched hydrocarbon chain radicals having one double bond including, but not limited to, ethenyl, 1- and 2-propenyl, 2-methyl-1-propenyl, 1- and 2-butenyl and the like.

The term "alkenyloxy" is used herein to mean —O-alkenyl, including, but not limited to, ethenyloxy, 1- and 2-propenyloxy, 2-methyl-1-propenyloxy, 1- and 2-butenyloxy and the like.

The term "alkoxyalkyl" is used herein to mean -alkyl-O-alkyl, including, but not limited to, methoxymethyl, ethoxymethyl, n-propoxymethyl, isopropoxymethyl, n-butoxymethyl, isobutoxymethyl, t-butoxymethyl and the like.

The term "cycloalkyl" is used herein to mean cyclic hydrocarbon radicals including, but not limited to, cyclopropyl, cyclobutyl, cyclopentyl, cyclohexyl and the like.

The term "halosubstituted alkyl" refers to an alkyl radical as described above substituted with one or more halogens including, but not limited to, chloromethyl, bromoethyl, trifluoromethyl and the like.

The term "halosubstituted alkoxy" is used herein to mean refers to an alkoxy radical as described above substituted with one or more halogens including, but not limited to, chloromethoxy, bromoethoxy, difluoromethoxy, trifluoromethoxy and the like.

The term "alkoxycarbonyl" is used herein to mean —COO-alkyl, including, but not limited to, methoxycarbonyl, ethoxycarbonyl, propoxycarbonyl and the like.

The term "aryl" is used herein to mean aromatic radicals including, but not limited to, phenyl, naphthyl, pyridyl, quinolyl, thienyl, furyl, benzothienyl, benzofuryl and the like.

The term "arylalkyl" is used herein to mean an alkyl radical which is substituted by aryl group including, but not limited to, benzyl, phenethyl, phenylpropyl, pyridylmethyl, thienylmethyl, furylmethyl and the like.

A preferred class of compounds includes those wherein n, $R^1$, $R^2$, $R^3$ and $R^4$ are as defined above and $R^5$, $R^6$, $R^7$ and $R^8$ are each hydrogen. These compounds have the general formula (II).

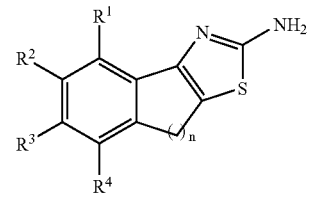

Also included within the scope of the invention are the ammonium halide derivatives as shown in the formula (III) illustrated below,

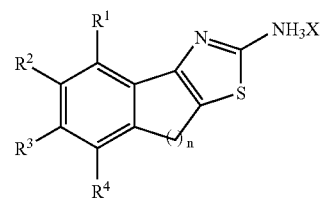

wherein, $R^1$, $R^2$, $R^3$ and $R^4$ are as defined above and X is halo.

Other preferred classes of compounds are those of formula (II) or (III) wherein $R^1$, $R^2$, $R^3$ and $R^4$ are each independently hydrogen, halo, alkyl, alkoxy, alkoxyalkyl, alkylamino, haloalkoxy, cycloalkyl, cycloalkoxy, cycloalkylamino, and wherein $R^1$ and $R^2$, $R^2$ and $R^3$, or $R^3$ and $R^4$, together with the carbon atoms to which they are attached, form a 5, 6 or 7-membered ring which may optionally include one or two heteroatoms selected from N, O and S and which may be optionally substituted with one or more substituents selected from halo, cyano, alkyl, alkenyl, alkoxy, alkenyloxy, alkoxyalkyl, halosubstituted alkyl, halosubstituted alkoxy, alkoxycarbonyl, aminocarbonyl and alkylthio.

Another preferred class of compounds are those of formula (II) or (III) wherein n is 1, X is I, $R^1$ and $R^4$ are hydrogen and $R^2$ and $R^3$ are each independently hydrogen, halo, alkyl, alkoxy, alkoxyalkyl, alkylamino, haloalkoxy, cycloalkyl, cycloalkoxy or cycloalkylamino.

Another preferred class of compounds are those wherein one of $R^1$, $R^2$, $R^3$ and $R^4$ is substituted or unsubstituted aryl or heteroaryl.

The compounds of the invention may be prepared by a number of synthetic methods. FIGS. 1-13 illustrate various reaction methods and classes of compounds within the scope of the present invention. FIGS. 14-17 illustrate representative examples of various 2-aminothiazole derivatives.

EXAMPLES

General Procedure: Allyl Ether Formation from hydroxy-indanone or hydroxy-tetralone A mixture of allyl bromide (15 mmol) and the hydroxy compound (10 mmol) in 2 N NaOH (10 mL) was stirred at room temperature and TLC (3:1 hexanes:ethyl acetate) was employed to monitor the reaction. Heating overnight at 70° C. accelerated sluggish reactions. The reaction mixture was diluted with water (25 mL) and extracted twice with ether (20 mL). The combined ether layers were washed with water and brine, separated and dried over $Na_2SO_4$. Vacuum evaporation yielded an oily residue that was purified by chromatography on a column of silica gel eluted with 5% then 10%, hexanes:ethyl acetate. Yield 83-94%. The compounds displayed spectral data in agreement with the reported data in literature.

6-Allyloxy-3,4-dihydro-2H-naphthalen-1-one: 88% (ref: Rodrigues, Denise C.; Fernandes, Sergio A.; Marsaioli, Anita J; Magn. Reson. Chem.; 38; 11; 2000; 970-974).

5-Allyloxy-indan-1-one: 83% (ref: Rodrigues, Denise C.; Fernandes, Sergio A.; Marsaioli, Anita J; Magn. Reson. Chem.; 38; 11; 2000; 970-974).

4-Allyloxy-indan-1-one: 94%, $^1$H-NMR (CDCl$_3$): δ 2.68 (t, J=6.6 Hz, 2H, CH$_2$), 6.07 (t, J=6.6 Hz, 2H, CH$_2$), 4.63 (dt, J=1.5, 4.8 Hz, 2H, CH$_2$), 5.32 (dd, J=1.5, 9.0 Hz, 1H, CH), 5.44 (dt, J=1.8, 15.6 Hz, 1H, CH), 6.07 (m, 1H, CH), 7.01 (dd, J=1.5, 6.6 Hz, 1H, ArH), 7.33 (m, 2H, ArH). GCMS: R$_f$=12.5 min., M$^+$=188 m/z.

General Procedure for Claisen Ether Rearrangement

Allyl ether (5 mmol) was dissolved in N,N-dimethyl aniline (15 mL) and the mixture was heated at reflux for 24-36 hours with monitoring by TLC (Hexanes:ethyl acetate 3:1). Upon completion of the reaction the mixture was cooled to room temperature and diluted with ethyl acetate (25 mL). The mixture was then washed successively with 1N HCl, water and brine, dried over $Na_2SO_4$ and evaporated to obtain thick oil. Column chromatography on silica gel eluted with hexanes:ethyl acetate 3:1 yielded pure products in 67-73% yields.

5-Allyl-6-hydroxy-3,4-dihydro2H-naphthale-1-one:Isolated as a mixture of regio-isomers (major>75% is desired isomer) (73%). $^1$H-NMR (CDCl$_3$): δ 1.94 (m, 2H, CH$_2$), 3.02 (t, J=5.7 Hz, 2H, CH$_2$) 3.48 (dt, J=1.5, 7.8 Hz, 2H, CH$_2$), 5.06-5.14 (m, 2H, =CH$_2$), 5.99 (m, 1H, =CH), 6.04 (brs, 1H, OH), 6.87 (d, J=8.1 Hz, 1H, ArH), 7.79 (d, J=8.4 Hz, 1H, ArH). $^{13}$C-NMR(CDCl$_3$): δ 24.4, 30.3, 36.5, 116.0, 116.2, 121.9, 123.8, 129.9, 134.5, 157.2, 160.2, 206.4. Mass (APCI): [M+H]$^+$=189 m/z.

4-Allyl-5-hydroxy-indane-1-one: (67%) $^1$H-NMR (CDCl$_3$): δ 2.69 (m, 2H, CH$_2$), 2.42 (t, J=6.0 Hz, 2H, CH$_2$), 2.70 (t, J=6.0 Hz, 2H, CH$_2$). 3.29 (d, J=5.7 Hz, 2H, CH$_2$), 4.72-4.96 (m, 2H, =CH2), 5.70-5.86 (m, 1H, =CH), 6.69 (d, J =8.7, 1H, ArH), 7.70 (d, J=8.7, 1H, ArH). GCMS: R$_t$ 15.6 min., M$^+$=202 m/z.

General Procedure for Cyclization of Phenol with Allyl Group

The compound (1 mmol) was dissolved in toluene (10 mL) and p-toluene sulfonic acid or polyphosphoric acid was added and the mixture was heated to reflux. TLC monitored the formation of the less polar product. When the reaction was complete the mixture was diluted with ether (20 mL) and washed with water. The organic layer was dried over $Na_2SO_4$ and evaporated to obtain crude product for purification by chromatography on silica gel eluted with hexanes:ethyl acetate, 9:1 to yield cyclized compound as a solid. Yield (70-86%).

2-Methyl-1,2,7,8-etrahydro-3-oxa-as-indancen-6-one: (70%) $^1$H-NMR (CDCl$_3$): δ 1.49 (d, J=6.6 Hz, 3H, CH$_3$), 2.64 (t, J=5.7 Hz, 2H, CH$_2$), 2.76 (dd, J=7.2, 15.3. Hz, 1H, CH$_2$), 2.93 (t, J=5.7 Hz, 2H, CH$_2$), 3.29 (dd, J=9.0, 15.6 Hz, 1H, CH$_2$), 5.06 (m, 1H, OCH), 6.74 (d, J=8.4, 1H, ArH), 7.57 (d, J=8.4, 1H, ArH). $^{13}$C-NMR(CDCl$_3$): δ 21.9, 24.2, 34.4, 36.4, 81.3, 109.5, 123.4, 125.0, 125.0, 130.5, 152.4, 165.2, 205.0. GCMS: R$_f$=14.5 min., M$^+$=188 m/z.

2-Methyl-1,7,8,9-tetrahydro-2H-naphtho[2,1-b]furan-6-one: (86%) $^1$H-NMR (CDCl3): δ 1.49 (d, J=6.6 Hz, 3H, CH$_3$), 2.10 (m, 2H, CH$_2$), 2.59 (t, J=7, 2H, CH$_2$), 2.76 (m, 3H, CH$_2$+CH), 3.25 (dd, J=9.0, 15.3 Hz, 1H, CH$_2$), 5.05 (m, 1H, OCH), 6.67 (d, J=8.7, 1H, ArH), 7.92 (d, J=8.7, 1H, ArH). $^{13}$C-NMR (CDCl$_3$): δ 22.0, 22.8, 27.1, 35.0, 38.6, 81.0, 108.2, 124.5, 126.1, 129.2, 141.6, 163.4, 196.6. Mass (APCI): [M+H]$^+$=203 m/z.

General Procedure for the Synthesis of 2-aminothiazole Derivatives

A mixture of ketone (1.0 mmol), thiourea (2.5 mmole) and iodine (1.1 mmol) in either dry DMF or ethanol was stirred for 3-5 hrs in an oil bath at 80-105° C. After cooling to room temperature the residue was triturated twice with 10 mL of ether, once with hot water and the solid product was filtered off, washed with water and dried. Crystallization from acetone-water or ethanol-water yielded solid samples. Yields ranged between 50 and 90%. A few of these compounds are reported in Chordia et al., Bioorg. Med. Chem. Lett., 12, 1563-1566, 2002.

NMR Data for Selected 2-aminothiazole Compounds a) 8H-3-Thia-1-aza-cyclopenta[a]inden-2-ylamine hydroiodide: $^1$H-NMR (DMSO-d$_6$): δ 3.75 (s, 2H, CH$_2$), 7.16 (t, J=7.8, 1H, ArH), 7.29 (t, J=7.2, 1H, ArH), 7.48 (t, J=6.6 Hz, 2H, ArH).

b) 6-Methoxy-8H-indeno[1,2-d]thiazol-2-amine hydroiodide: $^1$H-NMR (DMSO-d$_6$): δ 3.78 (s, 2H, CH$_2$), 3.79 (s, 3H, OCH$_3$), 6.79 (dd, J=2.4, 7.8 Hz, 1H, ArH), 7.07 (d, J=2.4 Hz, 1H, ArH), 7.42 (d, J=8.4 Hz, 1H), 8.5 (br s). $^{13}$C-NMR (DMSO-d$_6$): δ 31.5, 55.2, 103.8, 110.6, 125.6, 131.9, 137.6, 137.9, 154.7, 158.8, 159.5.

c) 7-Methyl-8H-indeno[1,2-d]thiazol-2-amine hydroiodide: $^1$H-NMR (DMSO-d$_6$): δ 2.36 (s, 3H, CH$_3$), 3.73 (s, 2H, CH$_2$), 7.07 (d, J=7.8 Hz, 1H, ArH), 7.39 (s, 1H, ArH), 7.41 (d, J=7.8 Hz, 1H, ArH), 9.0 (br s). $^{13}$C-NMR (DMSO-d$_6$): δ 21.1, 33.6, 118.8, 122.1, 124.8, 126.4, 132.9, 136.1, 142.3, 142.6, 173.9.

d) 5-Methyl-8H-indeno[1,2-d]thiazol-2-amine hydroiodide: $^1$H-NMR (DMSO-d$_6$): δ 2.33 (s, 3H, CH$_3$), 3.70 (s, 2H, CH$_2$), 7.09 (d, J=7.8 Hz, 1H, ArH), 7.27 (t, J=7.8, 1H, ArH), 7.40 (d, J=7.5 Hz, 1H, ArH), 9.0 (br s). $^{13}$C-NMR (DMSO-d$_6$): δ 18.0, 32.8, 116.0, 121.6, 127.0, 127.2, 132.4, 133.9, 143.8, 173.8.

e) 6-Bromo-8H-indeno[1,2,-d]thiazole-2-ylamine hydroiodide: $^1$H-NMR (DMSO-d$_6$): δ 3.89 (s, 2H, CH$_2$), 7.46 (d, J=8.1 Hz, 1H, ArH), 7.53 (dd, J=1.8, 8.1 Hz, 1H, ArH), 7.75 (d, J=1.8 Hz, 1H, ArH), 8.80 (brs, 2H, NH$_2$)

f) Acetic acid-2-amino-8H-indeno[1,2-d]thiazol-6-yl ester: $^1$H-NMR (DMSO-d$_6$): δ 2.25 (s, 3H, CH$_3$), 3.68 (s, 2H, CH$_2$), 7.01 (d, J=7.2 Hz, 1H, ArH), 7.17 (brs, 2H, NH$_2$), 7.22 (brs, 1H, ArH), 7.33 (d, J=7.8, 1H, ArH).

g) Acetic acid -2-amino-8H-indeno[1,2-d]thiazol-5-yl ester: $^1$H-NMR (DMSO-d$_6$): δ 2.33 (s, 3H, CH$_3$), 3.76 (s, 2H, CH$_2$), 7.01 (dd, J=1.2, 7.8 Hz, 1H, ArH), 7.44 (m, 2H, ArH), 8.52 (brs, 2H, NH$_2$).

h) 5,6-Dimethoxy-8H-indeno[1,2,-d]thiazole-2-ylamine hydroiodide: $^1$H-NMR (DMSO-d$_6$): δ 3.68 (s, 2H, CH$_2$), 3.77 (s, 3H, OCH$_3$), 3.78 (s, 3H, OMe), 7.20 (1H, CH, ArH), 7.25 (1H, s, ArH), 9.00 (brs, 2H, NH2). $^{13}$C-NMR (DMSO-d$_6$): δ 33.6, 55.6, 55.8, 102.4, 109.8, 119.1, 137.8, 147.6, 148.0, 173.7.

i) 5,6,7-Trimethoxy-8H-indeno[1,2-d]thiazol-2-ylamine-hydroiodide: $^1$H-NMR (DMSO-d$_6$): δ 3.73 (s, 2H, CH$_2$), 3.76 (s, 3H, OMe), 3.81 (s, 3H, OMe), 3.93 (s, 3H, OMe), 3.93 (s, 3H, OMe), 7.11 (s, 1H, ArH), 8.72 (brs, 2H, NH$_2$). $^{13}$C-NMR (DMSO-d$_6$): δ 34.0, 56.3, 60.6, 61.5, 106.3, 1 18.5, 119.2, 140.2, 141.2, 144.7, 152.7, 174.4.

j) 6,7,8-Trimethoxy-8H-indeno[1,2-d]thiazol-2-ylamine hydroiodide: $^1$H-NMR (DMSO-d$_6$): δ 3.73 (s, 2H, CH$_2$), 3.76 (s, 3H, OMe), 3.81 (s, 3H, OMe), 3.93 (s, 3H, OMe), 7.11 (s, 1H, ArH), 8.72 (brs, 2H, NH$_2$). $^{13}$C-NMR (DMSO-d$_6$): δ 31.4, 56.1, 60.2, 60.6, 98.6, 121.2, 128.2, 128.8, 139.6, 149.5, 153.2, 173.8.

k) Acetic acid-2-amino-4,5-dihydronaphtho[1,2-d]thiazole-7-yl ester hydroiodide: $^1$H-NMR (DMSO-d$_6$): δ 2.21 (s, 3H, CH3), 2.77 (t, J=7.8 Hz, 2H, CH$_2$), 2.99 (t, J=7.8 Hz, 2H, CH$_2$), 6.96 (d, J=8.4 Hz, 1H, ArH), 6.98 (s, 1H, ArH), 7.48 (d, J=8.4 Hz, 1H, ArH), 9.01 (brs, 2H, NH$_2$).

l) 5,6-Dihydro-4H-3-thia-1-aza-benzo[e]azulen-2-ylamine hydroiodide: $^1$H-NMR (DMSO-d$_6$): δ2.02 (m, 2H, CH$_2$), 2.77 (m, 4H, 2×CH$_2$), 7.29-7.39 (m, 3H, ArH), 7.56 (dd, J=1.2, 6.6 Hz, 1H).

m) 7-Octyloxy4,5-dihydronaphtho[1,2-d]thiazole-2-ylaminehydroiodide: $^1$H-NMR (DMSO-d$_6$): δ 0.81 (t, J=6.6, 3H, CH$_3$), 1.15-1.37 (m, 10H, 5×CH$_2$), 1.65 (m, 2H, CH$_2$), 2.72 (t, J=8.4, 2H, CH$_2$), 2.95 (t, J=8.4, 2H, CH$_2$), 3.90 (t, J=6.9, 2H, CH$_2$), 6.73 (dd, J=2.4, 8.4 Hz, 1H, ArH), 6.75 (d, J=2.4 Hz, 1H, ArH), 7.36 (d, J=8.4 Hz, 1H, ArH), 8.91 (br s, NH$_2$). $^{13}$C-NMR (DMSO-d$_6$+CDCl$_3$): δ 13.6, 20.6, 21.9, 25.3, 28.1, 28.5, 28.6, 31.1, 67.3, 111.6, 112.6, 114.8, 117.6, 122.5, 132.4, 135.9, 158.8, 168.9.

n) 7-Pentanoxy-4,5-dihydronaphtho[1,2-d]thiazole-2-ylamine hydroiodide: $^1$H-NMR (DMSO-d$_6$): δ 0.87 (t, J=6.6, 3H, CH$_3$), 1.29-1.42 (m, 4H, 2×CH$_2$), 1.65 (m, 2H, CH$_2$), 2.72 (t, J=8.1, 2H, CH$_2$), 2.95 (t, J=8.1, 2H, CH$_2$), 3.96 (t, J=6.6, 2H, CH$_2$), 6.87 (dd, J=2.4, 8.4 Hz, 1H, ArH), 6.89 (d, J=2.4 Hz, 1H, ArH), 7.44 (d, J=8.4 Hz, 1H, ArH), 8.98 (brs, NH$_2$). $^{13}$C-NMR (DMSO-d$_6$+CDCl$_3$): δ 13.9, 20.7, 21.8, 27.6, 28.0, 28.3, 67.5, 112.1, 113.6, 115.1, 118.2, 122.9, 132.8, 136.5, 158.7, 169.2.

o) 5-Methyl-4,5-dihydro-naphtho[1,2-d]thiazol-2-ylamine hydroiodide: $^1$H-NMR (DMSO-d$_6$): δ 1.21 (d, J=6.9, 3H, CH$_3$), 2.64 (dd, J=6.3, 16.8 Hz, 1H, CH$_2$), 2.95 (dd, J=6.8, 16.5 Hz, 1H, CH$_2$), 3.15 (m, 1H, CH), 7.20-7.35 (m, 3H, ArH), 7.54 (dd, J=1.8, 6.0 Hz, 1H, ArH), 8.80 (brs, NH$_2$). $^{13}$C-NMR (DMSO-d$_6$): δ 20.5, 28.0, 32.4, 115.6, 121.7, 124.6, 126.8, 127.3, 128.7, 132.6 139.4, 169.2.

p) 2-Methyl-1,2-dihydro-9H-3-oxa-8-thia-6-aza-cyclopenta[b]-as-indacen-7-ylamine hydroiodide: $^1$H-NMR (DMSO-d$_6$): δ 1.32 (d, J=6.3, 3H, CH$_3$), 2.80 (dd, J=7.5, 15.9 Hz, 1H, CH$_2$), 3.35 (dd, J=8.7, 15.9 Hz, 1H, CH$_2$), 4.95 (m, 1H, OCH), 6.73 (d, J=8.1 Hz, 1H, ArH), 7.12 (brs, 2H, NH$_2$), 7.31 (d, J=8.1 Hz, 1H, ArH).

q) 7-Methyl-7,8,9,10-tetrahydro-6-oxa-1-thia-3-aza-dicyclopenta[a,f]naphthalene-2-ylamine: $^1$H-NMR (DMSO-d$_6$): δ 1.38 (d, J=6.6, 3H, CH$_3$), 2.71-2.87 (m, 5H, 2×CH$_2$+H from CH$_2$), 3.29 (dd, J=9.1, 15.8 Hz, 1H, CH$_2$), 4.95 (m, 1H, OCH), 6.65 (d, J=8.1 Hz, 1H, ArH), 7.29 (d, J=8.1 Hz, 1H, ArH), 8.70 (brs, 2H, NH$_2$). $^{13}$C-NMR (DMSO-d$_6$): δ 20.2, 21.7, 24.9, 34.8, 79.8, 106.4, 112.6, 121.9, 126.5, 131.7, 159.3, 169.0 r) 4H-Chromeno[4,3-]thiazol-2-ylamine: $^1$H-NMR (DMSO-d$_6$): δ 5.27 (s, 2H, CH$_2$), 6.90 (dd, J=2.1, 6.9 Hz, 1H, ArH), 7.00 (t, J=7.8, 1H, ArH), 7.19 (t, J=7.5 Hz, 1H, ArH), 7.46 (d, J=7.5 Hz, 1H, ArH).

s) 6-Methoxy-8H-indeno[1,2-d]thiazol-2-amine hydroiodide: $^1$H-NMR (DMSO-d$_6$): δ 3.70 (s, 2H, CH$_2$), 3.76 (s, 3H, OCH$_3$), 6.82 (dd, J=2.4, 7.8 Hz, 1H), 7.37 (d, J=2.4 Hz, 1H), 7.42 (d, J=8.4 Hz, 1H), 9.5 (br s).

t) 6-Methyl-8H-indeno[1,2-d]thiazol-2-amine hydroiodide: $^1$H-NMR (DMSO-d$_6$): δ 2.35 (s, 3H, CH$_3$), 3.71 (s, 2H, CH$_2$), 7.07 (d, J=7.8 Hz, 1H), 7.39 (s, 1H), 7.41 (d, J=7.8 Hz, 1H), 9.0 (br s).

u) 5,6-Dimethyl-8H-indeno[1,2-d]thiazol-2-aminehydroiodide: $^1$H-NMR(DMSO-d$_6$): δ3.68 (s, 2H, CH$_2$), 3.77 (s, 3H, OCH$_3$), 3.78 (s, 3H, OCH$_3$), 7.20 (s, 1H), 7.25 (s, 1H), 9.0 (br s). $^{13}$C-NMR (DMSO-d$_6$): δ 33.6, 55.6, 55.8, 102.4, 109.8, 119.1, 137.8, 147.6, 148.0, 173.7.

v) 5-Bromo-8H-indeno[1,2-d]thiazol-2-amine hydroiodide: $^1$H-NMR (DMSO-d$_6$): δ 3.89 (s, 2H, CH$_2$), 7.47 (d, J=7.8 Hz,1H), 7.55 (dd, J=1.8, 7.8 Hz, 1H), 7.75 (d, J=1.2 Hz, 1H), 9.0 (br s).

NMR data for
6-(Aryl)-8H-indeno[1,2-d]-thiazol-2-ylamine hydro iodide:

(FIG. 9)

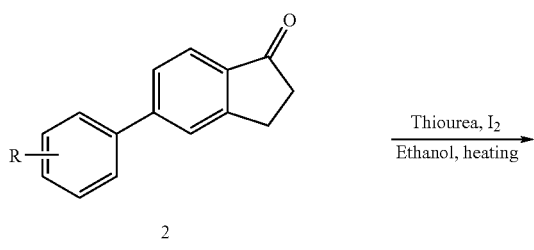

-continued

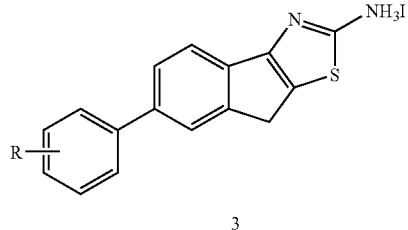

3 a) 6-(Phenyl)-8H-indeno[1,2-d]-thiazol-2-ylamine hydroiodide (MC-1-248) $^1$H-NMR (DMSO-$d_6$): δ 3.85 (s, 2H, CH$_2$), 7.35 (dt, J=1.2, 7.2 Hz, 1H, ArH), 7.46 (t, J=8.1 Hz, 2H, ArH), 7.60 (d, J=8.1 Hz, 2H, ArH), 7.65-7.70 (m, 3H, ArH), 7.5 (brs, 1H, ArH), 8.80 (brs, NH$_2$); $^{13}$C-NMR (DMSO-$d_6$): δ 33.9, 118.5, 122.5, 123.4, 125.6, 126.6, 127.4, 129.0, 132.5, 137.5, 140.0, 143.8, 146.2, 173.9.

b) 6-(4'-Methoxyphenyl)-8H-indeno[1,2-d]-thiazol-2-ylamine hydroiodide (MC-1-264) $^1$H-NMR (DMSO-$d_6$): δ 3.78 (s, 3H, OCH$_3$), 3.85 (s, 2H, CH$_2$), 7.02 (dd, J=2.1, 6.9 Hz, 2H, ArH), 7.60-7.65 (m, 4H, ArH), 7.81(brs, 1H, ArH)

c) 6-(3'-Methoxyphenyl)-8H-indeno [1,2-d]-thiazol-2-ylamine hydroiodide (MC-1-271) $^1$H-NMR (DMSO-$d_6$): δ 3.82 (s, 3H, OCH$_3$), 3.86 (s, 2H, CH$_2$), 6.92 (dt, J=1.8, 8.1 Hz, 1H, ArH), 7.21 (t, J=1.5 Hz, 1H, ArH), 7.25 (dd, J=0.9, 7.8 Hz, 1H, ArH), 7.37 (t, J=7.8 Hz, 1H, ArH), 7.61 (d, J=8.1 Hz, 1H, ArH), 7.69 (dd, J=1.5, 7.8 Hz, 1H, ArH), 7.87 (brs, 1H, ArH), 9.00 (brs, NH$_2$).

d) 6-(2'-Methoxyphenyl)-8H-indeno[1,2-d]-thiazol-2-ylamine hydroiodide (MC-1-270) $^1$H-NMR (DMSO-$d_6$): δ 3.76 (s, 3H, OCH$_3$), 3.82 (s, 2H, CH$_2$), 7.02 (t, J=7.5 Hz, 1H, ArH), 7.11 (d, J=7.5 Hz, 1H, ArH), 7.29 (dd, J=1.5, 7.5 Hz, 1H, ArH), 7.32 (dd, J=7.2, 8.1 Hz, 1H, ArH), 7.45 (dd, J=1.5, 8.1 Hz, 1H, ArH), 7.57 (d, J=8.1 Hz, 1H, ArH), 7.63 (brs, 1H, ArH), 9.00 (brs, NH$_2$); $^{13}$C-NMR (DMSO-$d_6$): δ 33.9, 55.5, 111.7, 117.7, 120.8, 122.1, 126.0, 128.0, 128.9, 129.6, 130.4, 131.6, 135.7, 143.1, 145.0, 156.1, 173.9 e) 6-(4'-Phenoxyphenyl)-8H-indeno[1,2-d]-thiazol-2-ylamine hydroiodide (MC-1-283) $^1$H-NMR (DMSO-$d_6$): δ 3.85 (s, 2H, CH$_2$), 7.04-7.10 (m, 4H, ArH), 7.16 (dt, J=0.9, 7.2 Hz, 1H, ArH), 7.38-7.45 (m, 2H, ArH), 7.58-7.75 (m, 4H, ArH), 7.84 (s, 1H, ArH), 8.99 (brs, NH$_2$).

f) 6-(3'-Nitroyphenyl)-8H-indeno [1,2-d]-thiazol-2-ylamine hydroiodide (MC-1-278) $^1$H-NMR (DMSO-$d_6$): δ 3.88 (s, 2H, CH$_2$), 7.66 (d, J=8.1 Hz, 1H, ArH), 7.75 (d, J=8.1 Hz, 1H, ArH), 7.81 (dd, J=1.8, 8.1 Hz, 1H, ArH), 8.00 (s, 1H, ArH), 8.19 (dt, J=2.4, 8.4 Hz, 1H, ArH), 8.46 (t, J=1.8, 1H, ArH), 8.98 (brs, NH$_2$).

g) 6-(4'-N,N-Dimethylphenyl)-8H-indeno[1,2-d]-thiazol-2-ylamine hydroiodide (MC-1-285) $^1$H-NMR (DMSO-$d_6$): δ 3.08 (s, 6H, NMe$_2$), 3.86 (s, 2H, CH$_2$), 7.24 (brd, 1H, ArH), 7.67 (ABd, J=7.5 Hz, 2H, ArH), 7.72 (d, J=8.4 Hz, 2H, ArH), 7.86 (s, 1H, ArH), 9.05 (brs, NH$_2$).

h) 6-(3',4'-Dimethoxyphenyl)-8H-indeno[1,2-d]-thiazol-2-ylamine hydroiodide (MC-1-284) $^1$H-NMR (DMSO-$d_6$): δ 3.82 (s, 3H, OCH$_3$), 3.86 (s, 2H, CH$_2$), 6.92 (dt, J=1.8, 8.1 Hz, 1H, ArH), 7.21 (t, J=1.5 Hz, 1H, ArH), 7.25 (dd, J=0.9, 7.8 Hz, 1H, ArH), 7.37 (t, J=7.8 Hz, 1H, ArH), 7.61 (d, J=8.1 Hz, 1H, ArH), 7.69 (dd, J=1.5, 7.8 Hz, 1H, ArH), 7.87 (brs, 1H, ArH), 9.00 (brs, NH$_2$).

i) 6-(3',4'-Methylenedioxyphenyl)-8H-indeno[1,2-d]-thiazol-2-ylamine hydroiodide (MC-1-277) $^1$H-NMR (DMSO-$d_6$): δ 3.84 (s, 2H, CH$_2$), 6.05 (s, 2H, OCH$_2$O), 6.99 (d, J=8.1 Hz, 1H, ArH), 7.17 (dd, J=1.8, 8.1 Hz, 1H, ArH), 7.26 (d, J=1.8 Hz, 1H, ArH), 7.60 (dd, J=1.5, 7.8 Hz, 2H, ArH), 7.80 (s, 1H, ArH), 9.10 (brs, NH$_2$).

j) 6-(3',4',5'-Trimethoxyphenyl)-8H-indeno[1,2-d]-thiazol-2-ylamine hydroiodide (MC-2-106) $^1$H-NMR (DMSO-$d_6$): δ 3.69 (s, 3H, OCH$_3$), 3.86 (s, 8H, CH$_2$+2×OCH$_3$), 6.94 (s, 2H, ArH), 7.22 (brs, NH$_3$), 7.60 (d, J=8.1, 1H, ArH), 7.71 (dd, J=1.8, 8.1 Hz, 1H, ArH), 7.91 (d, J=1.8 Hz, 1H, ArH).

k) 6-(1'-Naphthyl)-8H-indeno[1,2-d]-thiazol-2-ylamine hydroiodide (MC-2-107) $^1$H-NMR (DMSO-$d_6$): δ 3.89 (s, 2H, CH$_2$), 7.24 (m, 5H, ArH), 7.66 (s, 1H, ArH), 7.70 (d, J=8.4, 1H, ArH), 7.83 (brd, J=8.1, 1H, ArH), 7.96 (d, J=8.4, 1H, ArH), 8.10 (d, J=8.1, 1H, ArH).

l) 6-(3',4'-Dichlorophenyl)-8H-indeno[1,2-d]-thiazol-2-ylamine hydroiodide (MC-2-51) $^1$H-NMR (DMSO-$d_6$): δ 3.85 (s, 2H, CH$_2$), 7.63 (d, J=7.8 Hz, 1H, ArH), 7.69 (d, J=1.8, 7.8 Hz, 1H, ArH), 7.73 (dd, J=1.5, 7.8 Hz, 1H, ArH), 7.91 (d, J=0.9 Hz, 1H, ArH), 7.94 (t, J=1.2, 1H, ArH), m) 6-(3',5'-Dichlorophenyl)-8H-indeno[1,2-d]-thiazol-2-ylamine hydroiodide (MC-2-52) $^1$H-NMR (DMSO-$d_6$): δ 3.85 (s, 2H, CH$_2$), 7.57 (t, J=2.1 Hz, 1H, ArH), 7.61 (d, J=7.8 Hz, 1H, ArH), 7.75 (m, 3H, ArH), 7.94 (brs, 1H, ArH), n) 6-(3'-Furanyl)-8H-indeno[1,2-d]-thiazol-2-ylamine hydroiodide (MC-2-187) $^1$H-NMR (DMSO-$d_6$): δ 3.82 (s, 2H, CH$_2$), 6.99 (d, J=0.6 Hz, 1H, ArH), 7.54 (d, J=8.1 Hz, 1H, ArH), 7.62 (brd, J=8.1 Hz, 1H, ArH), 7.75 (dd, J=0.6 Hz, 1H, ArH), 7.81 (s, 1H, ArH), 8.21 (s, 1H, Arh), 9.00 (brs, NH$_2$).

o) 6-(3'-Thiophenyl)-8H-indeno[1,2-d]-thiazol-2-ylamine hydroiodide (MC-2-188) $^1$H-NMR (DMSO-$d_6$): δ 3.85 (s, 2H, CH$_2$), 7.65-7.61 (m, 2H, ArH), 7.65 (dd, J=3.0, 4.8 Hz, 1H, ArH), 7.74 (dd, J=1.2, 7.8 Hz, 1H, ArH), 7.69 (dd, J=1.5, 7.8 Hz, 1H, ArH), 7.89 (dd, J=1.5, 6.0 Hz, 1H, ArH), 7.93 (brs, 1H, ArH), 9.04 (brs, NH$_2$); $^{13}$C-NMR (DMSO-$d_6$): δ 34.0, 118.4, 120.8, 122.1, 122.8, 124.9, 127.2, 131.7, 132.6, 141.2, 143.0, 146.1, 173.9.

Figure 11:
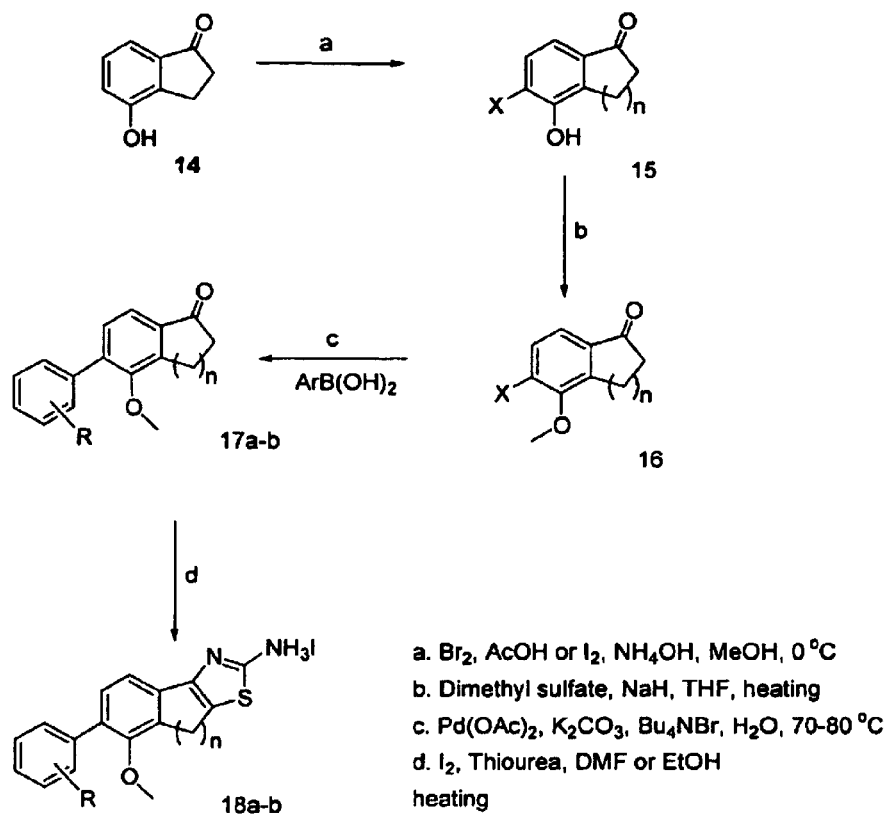
Figure 12:
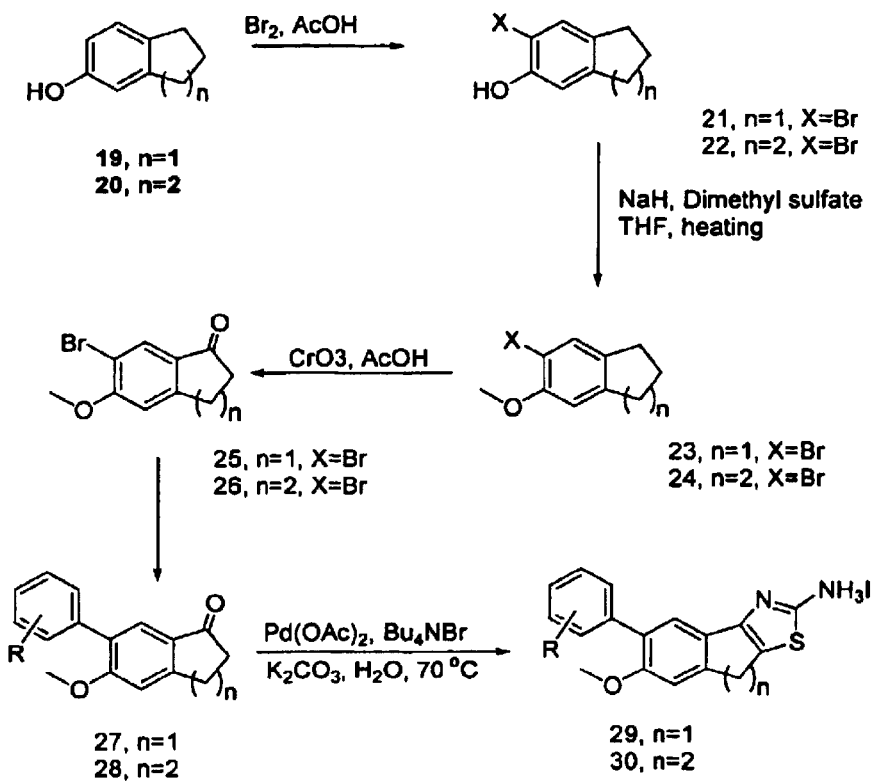
Figure 15:
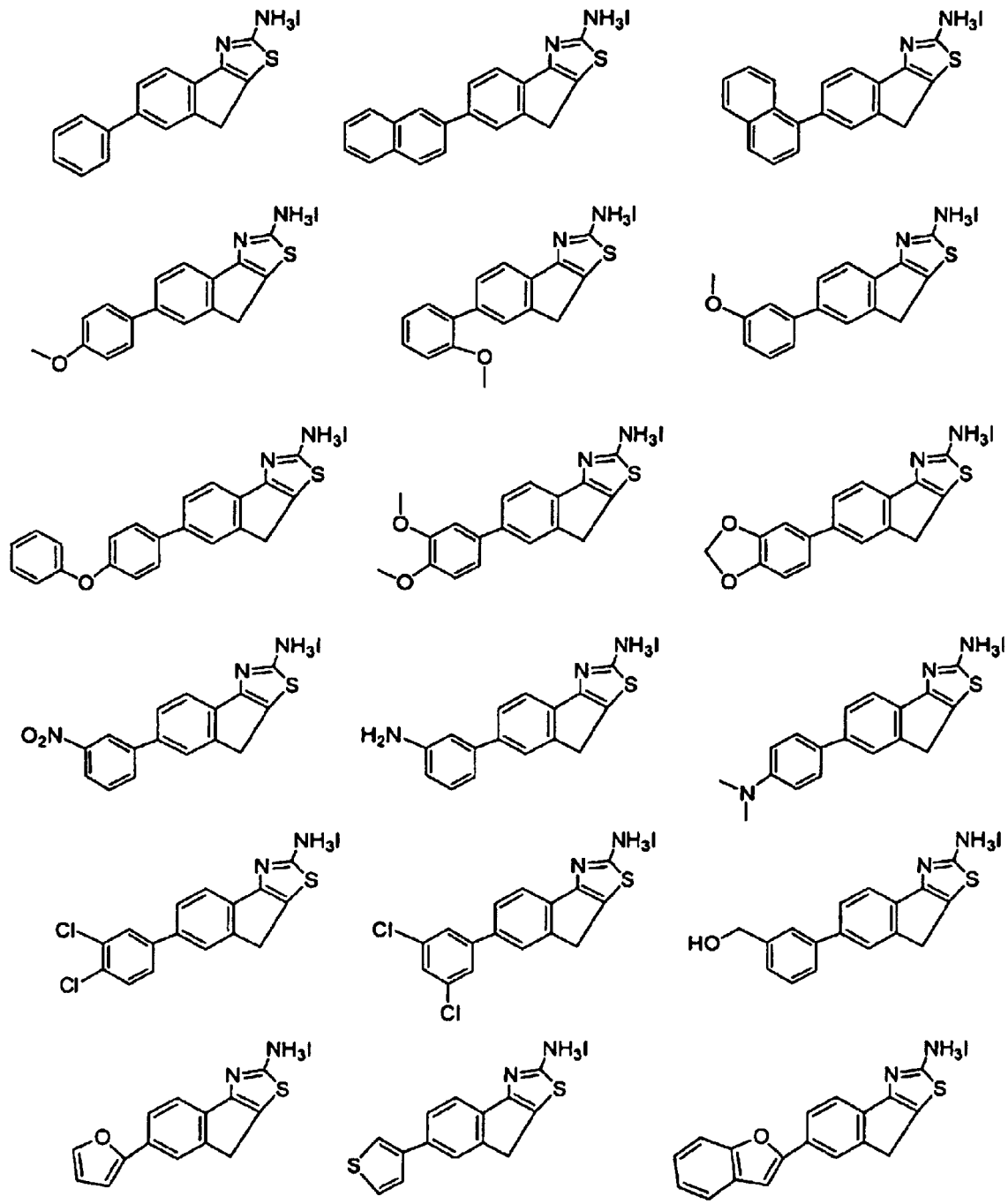
Figure 16:
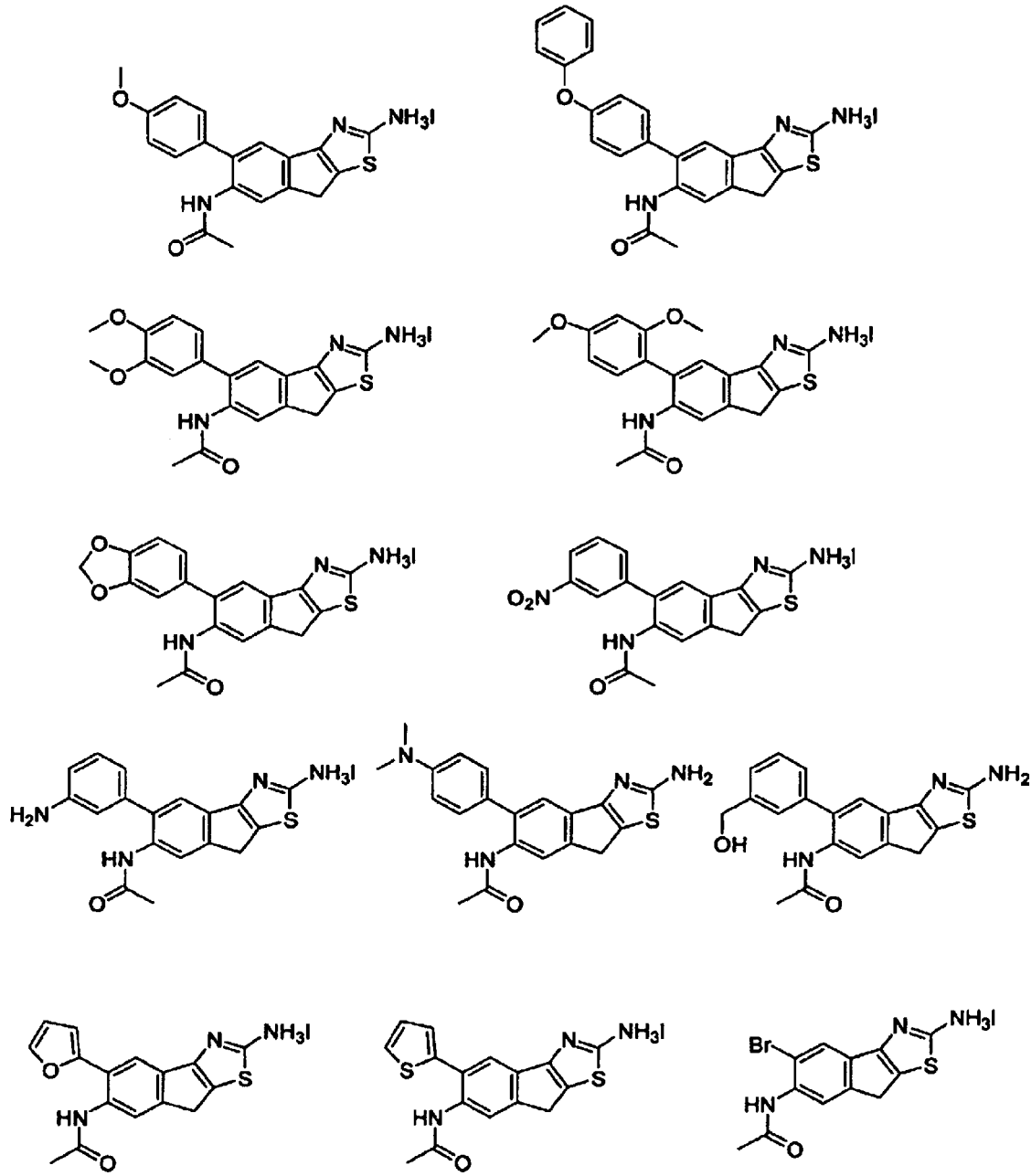
Figure 17:
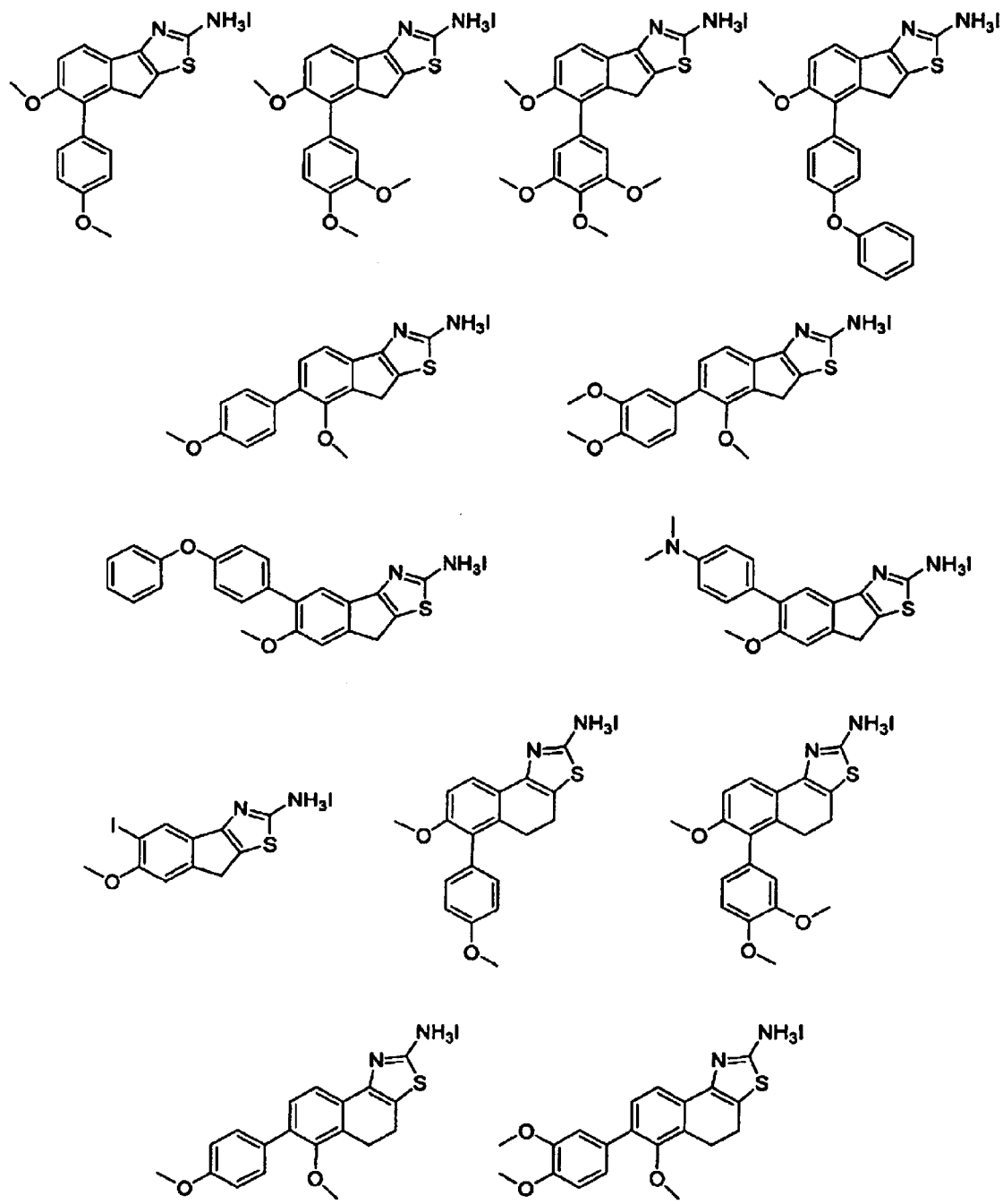

NMR Data for Various Compounds Produced by the Schemes Shown in FIGS. 10, 11 and 12
(Compounds 10-13, 17, 18, 27 and 29)

a) 4-(3',4'-Dimethoxyphenyl)-5-methoxy-indan-1-one (MC-2-63) $^1$H-NMR (CDCl$_3$): δ 2.63 (m, 2H, CH$_2$), 2.90 (t, J=5.7 Hz, 2H, CH$_2$), 3.86 (s, 3H, OCH$_3$), 3.88 (s, 3H, OCH$_3$), 3.93 (s, CH$_3$, OMe), 6.84 (d, J=1.8 Hz, 1H, ArH), 6.89 (dd, J=1.8, 8.1 Hz, 1H, ArH), 6.97 (d, J=8.4 Hz, 1H, ArH), 7.04 (d, J=8.4 Hz, 1H, ArH), 7.78 (d, J=8.1 Hz, 1H, ArH); $^{13}$C-NMR (CDCl$_3$): δ 25.3, 36.5, 55.8, 55.9, 56.2, 110.8, 111.0, 112.9, 121.8, 124.4, 127.3, 128.0, 130.3, 148.3, 148.6, 155.7, 161.7, 205.7; GCMS: R$_t$=21.6 min., M$^+$=298 m/z.

b) 4-(4'-Methoxyphenyl)-5-methoxy-indan-1-one (MC-2-64) $^1$H-NMR (CDCl$_3$): δ 2.61 (m, 2H, CH$_2$), 2.89 (t, J=5.7 Hz, 2H, CH$_2$), 3.84 (s, 3H, OCH$_3$), 3.85 (s, 3H, OCH$_3$), 6.99 (d, J=8.4 Hz, 2H, ArH), 7.01 (dd, J=1.8, 8.1 Hz, 1H, ArH), 7.03 (d, J=8.7 Hz, 1H, ArH), 7.25 (d, J=8.4 Hz, 2H, ArH), 7.77 (d, J=8.7 Hz, 1H, ArH); $^{13}$C-NMR (CDCl$_3$): δ 25.2, 36.5, 55.1, 56.1, 110.7, 113.7×2, 124.2, 126.9, 127.9, 130.3, 130.6×2, 155.7, 158.7, 161.7, 205.8; GCMS: R$_t$19.5 min., M$^+$=268 m/z.

c) 4-(3',4',5'-Trimethoxyphenyl)-5-methoxy-indan-1-one (MC-2-194) $^1$H-NMR (CDCl$_3$): δ 2.63 (m, 2H, CH$_2$), 2.92 (t, J=6.3 Hz, 2H, CH$_2$), 3.86 (s, 6H, 2×OCH$_3$), 3.87 (s, 3H, OCH$_3$), 3.91 (s, 3H, OCH$_3$), 6.51 (s, 1H, ArH), 7.04 (d, J=8.7 Hz, 1H, ArH), 7.79 (d, J=8.7 Hz, 1H, ArH); $^{13}$C-NMR (CDCl$_3$): δ 25.3, 36.4, 55.7, 56.0×2, 60.7, 106.5×2, 110.8, 124.5, 128.2, 130.3, 137.0, 153.0×2, 155.6, 161.5, 205.7: GCMS: R$_t$18.1 min., M$^+$=328 m/z.

d) 4-(4'-Phenoxy-phenyl)-5-methoxy-indan-1-one (MC-2-195) $^1$H-NMR (CDCl$_3$): δ 2.63 (m, 2H, CH$_2$), 2.91 (t, J=6.3 Hz, 2H, CH$_2$), 3.86 (s, 3H, OCH$_3$), 7.02-7.15 (m, 6H, ArH), 7.27 (dd, J=2.1, 8.7 Hz, 2H, ArH), 7.38 (t, J=8.1 Hz, 2H, ArH), 7.79 (d, J=8.4 Hz, 1H, ArH); $^{13}$C-NMR (CDCl$_3$): δ 25.2, 36.4, 56.0, 110.7, 118.0×2, 119.3×2, 123.4, 124.4, 127.5, 129.3, 129.6×2, 130.2, 130.9×2, 155.5, 156.5, 156.6, 161.5, 205.6; GCMS: R$_t$25.7 min., M$^+$=330 m/z.

e) 4-(4'-N,N-Dimethyl-phenyl)-5-methoxy-indan-1-one (MC-2-199) $^1$H-NMR (CDCl$_3$): δ 2.62 (m, 2H, CH$_2$), 2.94 (t, J=6.3 Hz, 2H, CH$_2$), 3.01 (s, 6H, NCH$_3$×2), 3.84 (s, 3H, OMe), 6.81 (d, J=8.7 Hz, 2H, ArH), 7.02 (d, J=8.4 Hz, 1H, ArH), 7.22 (d, J=8.7 Hz, 2H, ArH), 7.75 (d, J=8.4 Hz, 1H, ArH); $^{13}$C-NMR (CDCl$_3$): δ 25.3, 36.5, 40.3 2, 56.0, 110.7, 111.9×2, 122.2, 123.7, 130.2×2, 149.5, 155.8, 161.8, 206.0; GCMS: R$_t$=17.1 min., M$^+$=281 m/z.

f) 5-Methoxy-6-(4'-phenoxy-phenyl)-indan-1-one (MC-2-207) $^1$H-NMR (CDCl$_3$): δ 2.70 (m, 2H, CH$_2$), 3.15 (t, J=6.0 Hz, 2H, CH$_2$), 3.91 (s, 3H, OCH$_3$), 6.99-7.10 (m, 5H, ArH), 7.13 (t, J=8.7 Hz, 1H, ArH), 7.36 (t, J=8.1 Hz, 2H, ArH), 7.46 (d, J=8.4 Hz, 2H, ArH), 7.71 (s, 1H, ArH).

g) 5-Methoxy-6-(4'-N,N-dimethyl-phenyl)-indan-1-one (MC-2-208) $^1$H-NMR (CDCl$_3$): δ 2.69 (m, 2H, CH$_2$), 2.98 (s, 6H, NCH$_3$×2), 3.12 (t, J=6.3 Hz, 2H, CH$_2$), 3.89 (s, 3H, OMe), 6.77 (d, J=8.7 Hz, 2H, ArH), 6.95 (s, 1H, ArH), 7.02 (d, J=8.4 Hz, 1H, ArH), 7.42 (d, J=8.7 Hz, 2H, ArH), 7.93 (d, J=8.4 Hz, 1H, ArH).

h) 5-Methoxy-6-(3',4'-dimethoxyphenyl)-tetral-1-one (MC-2-69) $^1$H-NMR (CDCl$_3$): δ 2.15 (m, 2H, CH$_2$), 2.65 (t, J=6.9 Hz, 2H, CH$_2$), 3.02 (t, J=6.0 Hz, 2H, CH$_2$), 3.41 (s, 3H, OMe), 3.91 (s, 3H, OCH$_3$), 3.93 (s, 3H, OCH$_3$), 6.95 (d, J=8.4 Hz, 1H, ArH), 7.14 (dd, J=2.1, 8.1 Hz, 1H, ArH), 7.21 (d, J=2.1 Hz, 1H, ArH), 7.31 (d, J=8.1 Hz, 1H, ArH), 7.87 (d, J=8.1 Hz, 1H, ArH); $^{13}$C-NMR (CDCl$_3$): δ 22.6, 23.2, 38.5, 55.6, 55.7, 59.7, 110.8, 111.8, 121.1, 122.6, 128.4, 130.1, 132.5, 138.2, 138.9, 148.4, 148.6, 154.5, 197.7; GCMS: R$_t$=22.5 min., M$^+$=312 m/z.

i) 5-Methoxy-6-(4'-methoxyphenyl)-tetral-1-one (MC-2-70) $^1$H-NMR (CDCl$_3$): δ 2.15 (m, 2H, CH$_2$), 2.65 (t, J=7.2 Hz, 2H, CH$_2$), 3.02 (t, J=6.0 Hz, 2H, CH$_2$), 3.40 (s, 3H, OMe), 3.86 (s, 3H, OCH$_3$), 6.98 (d, J=8.7 Hz, 1H, ArH), 7.30 (d, J=8.1 Hz, 1H, ArH), 7.55 (d, J=8.7 Hz, 2H, ArH), 7.87 (d, J=8.1 Hz, 1H, ArH); GCMS: R$_t$=20.3 min., M$^+$=282 m/z.

j) 6-Methoxy-5-(4'-phenoxyphenyl)-tetral-1-one (MC-2-97) $^1$H-NMR (CDCl$_3$): δ 1.99 (m, 2H, CH$_2$), 2.61 (q, J=7.5 Hz, 4H, 2×CH$_2$), 3.80 (s, 3H, OCH$_3$), 6.95 (d, J=8.7 Hz, 1H, ArH), 7.07-7.17 (m, 7H, ArH), 7.36 (dt, J=1.8, 8.4 Hz, 2H, ArH), 8.15 (d, J=9.0 Hz, 1H, ArH).

k) 6-Methoxy-5-(4'-methoxyphenyl)-tetral-1-one (MC-2-98) $^1$H-NMR (CDCl$_3$): δ 1.97 (m, 2H, CH$_2$), 2.59 (q, J=5.7 Hz, 4H, 2×CH$_2$), 3.79 (s, 3H, OCH$_3$), 3.86 (s, 3H, OMe), 6.94 (d, J=8.7 Hz, 1H, ArH), 6.98 (d, J=9.0 Hz, 2H, ArH), 7.12 (d, J=9.0 Hz, 2H, ArH), 8.13 (d, J=9.0 Hz, 1H, ArH); $^{13}$C-NMR (CDCl$_3$): δ 23.1, 28.2, 38.5, 55.0, 55.7, 108.8, 113.6×2, 126.2, 128.2, 128.7, 128.9, 130.9×2, 144.6, 158.5, 160.8, 197.7; GCMS: R$_t$=26.7 min., M$^+$=282 m/z.

l) 6-Methoxy-5-(4'-methoxyphenyl)-tetral-1-one (MC-2-99) $^1$H-NMR (CDCl$_3$): δ 1.98 (m, 2H, CH$_2$), 2.60 (q, J=5.7 Hz, 4H, 2×CH$_2$), 3.79 (s, 3H, OCH$_3$), 3.87 (s, 3H, OMe), 3.92 (s, 3H, OMe), 6.71 (d, J=1.8 Hz, 1H, ArH), 6.74 (dd, J=1.8, 8.4 Hz, 1H, ArH), 6.94 (d, J=8.4 Hz, 2H, ArH), 8.13 (d, J=8.7 Hz, 1H, ArH); $^{13}$C-NMR (CDCl$_3$): δ 23.0, 28.1, 38.5, 55.6, 55.7, 108.8, 110.7, 112.9, 121.9, 126.1, 128.5, 128.7, 129.0, 144.6, 147.9, 148.5, 160.7, 197.6; GCMS: R$_t$=29.7 min., M$^+$=312 m/z.

m) 6-Methoxy-7-(3',4'-dimethoxyphenyl)8H-indeno[1,2-d]-thiazol-2-ylamine hydroiodide (MC-2-67) $^1$H-NMR (DMSO-d$_6$): δ 3.56 (s, 2H, CH$_2$), 3.72 (s, 3H, OCH$_3$), 3.73 (s, 3H, OCH$_3$), 3.78 (s, 3H, OCH$_3$), 6.88 (dd, J=1.8, 8.4 Hz, 1H, ArH), 6.93 (d, J=1.8 Hz, 1H, ArH), 7.00 (d, J=8.4 Hz, 1H, ArH), 7.18 (d, J=8.4 Hz, 1H, ArH), 7.51 (d, J=8.1 Hz, 1H, ArH), 9.10 (brs, NH$_3$); $^{13}$C-NMR (DMSO-d$_6$): δ 33.6, 55.5, 55.6, 56.0, 110.1, 111.6, 113.3, 117.7, 119.6, 121.8, 126.2, 127.7, 128.4, 143.3, 145.7, 148.0, 148.4, 155.1, 173.8.

n) 6-Methoxy-7-(4'-methoxyphenyl)-8H-indeno[1,2-d]-thiazol-2-ylamine hydroiodide (MC-2-68) $^1$H-NMR (DMSO-d$_6$): δ 3.53 (s, 2H, CH$_2$), 3.71 (s, 3H, OCH$_3$), 3.79 (s, 3H, OCH$_3$), 6.98 (dd, J=2.7, 8.7 Hz, 2H, ArH), 7.10 (d, J=8.4 Hz, 1H, ArH), 7.29 (dd, J=3.0, 8.7 Hz, 2H, ArH), 7.51 (d, J=8.4 Hz, 1H, ArH), 9.20 (brs, NH$_3$); $^{13}$C-NMR (DMSO-d$_6$): δ 33.6, 55.1, 56.0, 110.1, 111.6, 113.7×2, 117.8, 119.5, 126.0, 127.3, 128.1, 130.7×2, 142.9, 145.6, 155.1, 158.5, 173.9.

o) 6-Methoxy-7-(3+,4',5 '-trimethoxyphenyl)-8H-indeno[1,2-d]-thiazol-2-ylamine hydroiodide (MC-2-196) $^1$H-NMR (DMSO-d$_6$): δ 3.58 (s, 2H, CH$_2$), 3.70 (s, 3H, OCH$_3$), 3.74 (s, 3H, OCH$_3$), 3.75 (s, 6H, 2×Ome), 6.98 (dd, J=2.7, 8.7 Hz, 2H, ArH), 6.63 (s, 2H, ArH), 7.11 (d, J=8.1 Hz, 1H, ArH), 7.51 (d, J=8.1 Hz, 1H, ArH), 9.00 (brs, NH$_3$); $^{13}$C-NMR (DMSO-d$_6$): δ 33.6, 56.0×2, 60.0, 106.6, 110.1, 117.9, 119.7, 126.0, 128.5, 130.9, 136.5, 142.9, 145.6, 152.7, 155.0, 173.8.

p) 6Methoxy-7-(4'-phenoxy-phenyl)-8H-indeno[1,2-d]-thiazol-2-ylamine hydroiodide (MC-2-197) $^1$H-NMR (DMSO-d$_6$): δ 3.55 (s, 2H, CH$_2$), 3.73 (s, 3H, OCH$_3$), 7.00-7.14 (m, 6H, ArH), 7.17 (t, J=7.2 Hz, 1H, ArH), 7.38-7.46 (m, 3H, ArH), 7.52 (d, J=8.4 Hz, 1H, ArH), 9.00 (brs, NH$_3$); $^{13}$C-NMR (DMSO-d$_6$): δ 33.6, 56.0, 110.1, 117.8×2, 118.0, 119.1×2, 123.8, 126.0, 127.6, 130.1×2, 131.2×2, 142.8, 145.5, 155.0, 156.1, 156.2, 173.8.

q) 6-Methoxy-7-(4'-N,N-dimethylamino-phenyl)-8H-indeno[1,2-d]-thiazol-2-ylamine (neutral compound) (MC-2-201) $^1$H-NMR (DMSO-d$_6$): δ 2.92 (s, 6H, NCH$_{3×2}$), 3.43 (s, 2H, CH$_2$), 3.67 (s, 3H, OCH$_3$), 6.75 (d, J=8.7 Hz, 2H, ArH), 6.97 (d, J=8.4 Hz, 1H, ArH), 7.20 (d, J=8.7 Hz, 2H, ArH), 7.24 (d, J=8.4 Hz, 1H, ArH).

r) 5-Methoxy-6-(3',4'-dimethoxypheny)-tetralone-aminothiazole (MC-2-71) $^1$H-NMR (DMSO-d$_6$): δ 2.83 (t, J=7.8 Hz, 2H, CH$_2$), 3.05 (t, J=7.8 Hz, 2H, CH$_2$), 3.35 (s, 3H, OCH$_3$), 3.78 (s, 3H, OCH$_3$), 3.79 (s, 3H, OCH$_3$), 7.03 (d, J=8.1 Hz, 1H, ArH), 7.11 (dd, J=2.1, 8.1 Hz, 1H, ArH), 7.16 (d, J=2.1 Hz, 1H, ArH), 7.34 (d, J=7.8 Hz, 1H, ArH), 7.38 (d, J=8.1 Hz, 1H, ArH), 8.80 (brs, NH$_3$); $^{13}$C-NMR (DMSO-d$_6$): δ 20.4, 21.3, 55.4, 55.5, 59.9, 111.6, 112.2, 117.2, 117.85, 117.89, 120.8, 126.4, 127.8, 128.8, 129.9, 134.2, 148.2, 148.4, 154.5, 169.0.

s) 5-Methoxy-6-(4'-methoxypheny)-tetralone-aminothiazole (MC-2-72) $^1$H-NMR (DMSO-d$_6$): δ 2.84 (t, J=7.8 Hz, 2H, CH$_2$), 3.05 (t, J=8.1 Hz, 2H, CH$_2$), 3.32 (s, 3H, OCH$_3$), 3.79 (s, 3H, OCH$_3$), 7.01 (dd, J=2.1, 6.9 Hz, 2H, ArH), 7.30 (d, J=7.5 Hz, 1H, ArH), 7.38 (d, J=7.8 Hz, 1H, ArH), 7.50 (dd, J=2.1, 6.6 Hz, 2H, ArH), 8.70 (brs, NH$_3$); $^{13}$C-NMR (DMSO-d$_6$): δ 20.4, 21.3, 55.1, 59.8, 113.8×2, 117.2, 117.9, 127.8, 128.7, 129.71, 129.79×2, 134.1, 154.5, 158.6, 169.0.

t) 6-Methoxy-5-(4'-methoxypheny)-tetralone-aminothiazole (MC-2-101) $^1$H-NMR (DMSO-d$_6$): δ 2.63 (brs, 4H, 2×CH$_2$), 3.67 (s, 3H, OCH$_3$), 3.77 (s, 3H, OCH$_3$), 6.97 (d, J=8.7 Hz, 2H, ArH), 7.05 (d, J=8.2 Hz, 1H, ArH), 7.08 (d, J=8.1 Hz, 1H, ArH), 7.53 (d, J=8.4 Hz, 1H, ArH), 8.90 (brs, NH$_3$).

u) 6-Methoxy-5-(3,4'-dimethoxypheny)-tetralone-aminothiazole (MC-2-102) $^1$H-NMR (DMSO-d$_6$): δ 2.64 (m, 4H, 2×CH$_2$), 3.68 (s, 3H, OCH$_3$), 3.71 (s, 3H, OCH$_3$), 3.77 (s, 3H, OCH$_3$), 6.67 (dd, J=2.1, 8.1 Hz, 1H, ArH), 6.71 (d, J=1.8 Hz, 1H, ArH), 6.98 (d, J=8.1 Hz, 1H, ArH), 7.04 (d, J=8.4 Hz, 1H, ArH), 7.53 (d, J=8.4 Hz, 1H, ArH), 8.80 (brs, NH$_3$).

v) 5-Iodo-6-methoxy-8H-indeno[1,2-d]-thiazol-2yl-amine hydroiodide (MC-2-216) $^1$H-NMR (DMSO-d$_6$): δ 3.76 (s, 2H, CH$_2$), 3.86 (s, 3H, OMe), 7.42 (s, 1H, ArH), 7.71 (s, 1H, ArH), 9.00 (brs, NH$_3$).

NMR Data for 5-N-Acetamido-6-Aryl-indan-1-ones (FIG. 13)

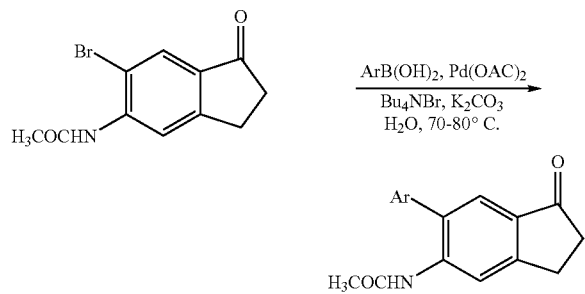

Ar = substituted aromatic and heteroaromatic substituent a) 5-N-Acetamido-6-(4'-methoxy-phenyl)-indan-1-one (MC-2-21) $^1$H-NMR (CDCl$_3$): δ 2.06 (s, 3H, NHCOCH$_3$), 2.71 (m, J=6.0 Hz, 2H, CH$_2$), 3.17 (t, J=6.0 Hz, 2H, CH$_2$), 3.88 (s, 3H, OCH$_3$), 7.03 (dd, J=1.8, 8.4, Hz, 2H, ArH), 7.28 (dd, J=1.8, 8.4 Hz, 2H, ArH), 7.42 (s, 1H, ArH), 7.59 (s, 1H, ArH), 8.56 (s, 1H, ArH); $^{13}$C-NMR (CDCl$_3$): δ 24.8, 25.7, 36.4, 55.2, 114.6×2, 117.0, 125.1, 128.8×2, 130.3, 130.8, 132.3, 140.7, 155.8, 159.6, 168.3, 205.7; GCMS: R$_t$=25.2 min., M$^+$=295 m/z.

b) 5-N-Acetamido-6-(4'-phenoxy-phenyl)-indan-1-one (MC-2-23) $^1$H-NMR (CDCl$_3$): δ 2.08 (s, 3H, NHCOCH$_3$), 2.71 (m, 2H, CH$_2$), 3.18 (t, J=6.0 Hz, 2H, CH$_2$), 7.08-7.13 (m, 3H, ArH), 7.16 (t, J=Hz, 1H, ArH), 7.28-7.32 (m, 3H, ArH), 7.38-7.43 (m, 3H, ArH), 7.62 (s, 1H, ArH), 8.57 (s, 1H, ArH); $^{13}$C-NMR (CDCl$_3$): δ 24.7, 25.6, 36.2, 117.4, 118.6×2, 119.4×2, 123.9, 125.0, 129.2×2, 130.5×2, 131.1, 132.3, 140.5, 155.8, 157.7, 168.3, 205.5 c) 5-N-Acetamido-6-(3',4'-dimethoxy-phenyl)-indan-1-one (MC-2-12) $^1$H-NMR (CDCl$_3$): δ 2.07 (s, 3H, NHCOCH$_3$), 2.71 (m, J=6.0 Hz, 2H, CH$_2$), 3.17 (t, J=6.0 Hz, 2H, CH$_2$), 3.89 (s, 3H, OCH$_3$), 3.95 (s, 3H, OCH$_3$), 6.83 (d, J=1.8 Hz, 1H, ArH), 6.90 (dd, J=2.1, 8.1 Hz, 1H, ArH), 6.99 (d, J=8.1 Hz, 1H, ArH), 7.51 (s, 1H, ArH), 7.62 (s, 1H, ArH), 8.59 (s, 1H, ArH); $^{13}$C-NMR (CDCl$_3$): δ 24.8, 25.7, 36.3, 55.7, 55.8, 111.4, 112.1, 116.9, 121.2, 124.8, 129.1, 130.8, 132.1, 140.6, 148.9, 149.4, 155.8, 168.2, 205.6; GCMS: R$_t$=29.05 min., M$^+$=325 m/z.

d) 5-N-Acetamido-6-(3',4'-methylenedioxy-phenyl)-indan-1-one (MC-2-56) $^1$H-NMR (CDCl$_3$): δ 2.08 (s, 3H, NHCOCH$_3$), 2.70 (m, J=6.0 Hz, 2H, CH$_2$), 3.16 (t, J=6.0 Hz, 2H, CH$_2$), 6.06 (s, 2H, OCH$_2$O), 6.71-6.81 (m, 2H, ArH), 6.93 (d, J=8.1 Hz, 1H, ArH), 7.45 (brs, 1H, ArH), 7.58 (s, 1H, ArH), 8.57 (s, 1H, ArH); $^{13}$C-NMR (CDCl$_3$): δ 24.9, 25.8, 36.4, 101.4, 108.9, 109.5, 117.1, 122.6, 125.1, 130.4, 130.7, 132.3, 140.7, 147.8, 148.4, 155.9, 168.3, 205.6; GCMS: R$_t$=27.4 min., M$^+$=309 m/z.

e) 5-N-Acetamido-6-(2',4'-dimethoxyphenyl)-indan-1-one (MC-2-57) $^1$H-NMR (CDCl$_3$): δ 2.03 (s, 3H, NHCOCH$_3$), 2.68 (m, J=6.0 Hz, 2H, CH$_2$), 3.15 (t, J=6.0 Hz, 2H, CH$_2$), 3.76 (s, 3H, OCH$_3$), 3.86 (s, 3H, OCH$_3$), 6.59 (d, J=0.6 Hz, 1H, ArH), 6.60 (d, J=8.1 Hz, 1H, ArH), 7.46 (brs, 1H, ArH), 7.56 (s, 1H, ArH), 8.41 (brs, 1H, NH).

f) 5-N-Acetamido-6-(3'-nitro-phenyl)-indan-1-one (MC-2-32) $^1$H-NMR (CDCl$_3$): δ 2.08 (s, 3H, NHCOCH$_3$), 2.74 (m, J=6.0 Hz, 2H, CH$_2$), 3.21 (t, J=6.0 Hz, 2H, CH$_2$), 7.10 (brs, 1H, ArH), 7.64 (s, 1H, ArH), 7.73 (dd, J=1.2, 2.1 Hz, 1H, ArH), 8.27 (dd, J=1.2, 2.1 Hz, 1H, ArH), 8.33 (m, 1H, ArH), 8.52 (s, 1H, ArH); $^{13}$C-NMR (CDCl$_3$): δ 24.6, 25.8, 36.4, 119.0, 123.2, 124.1, 125.3, 129.3, 130.3, 133.0, 135.3, 138.9, 140.1, 148.6, 156.8, 168.5, 205.4 g) 5-N-Acetamido-6-(3'-phenyl-methylalcohol)-indan-1-one (MC-2-58) $^1$H-NMR (CDCl$_3$): δ 2.01 (s, 3H, NHCOCH$_3$), 2.64 (m, J=6.0 Hz, 2H, CH$_2$), 3.11 (t, J=6.0 Hz, 2H, CH$_2$), 4.70 (s, 2H, HOCH$_2$), 7.19 (dd, J=1.8, 8.4 Hz, 1H, ArH), 7.32 (s, 1H, ArH), 7.36-7.46 (m, 2H, ArH), 7.50 (brs, 1H, ArH), 7.53 (s, 1H, ArH), 8.50 (s, 1H, ArH); $^{13}$C-NMR (CDCl$_3$): δ 24.7, 25.8, 36.4, 64.5, 117.4, 125.1, 126.9, 127.7, 128.0, 129.3, 131.1, 132.4, 137.0, 140.5, 142.4, 156.2, 168.6, 206.1.

h) 5-N-Acetamido-6-(4'-N,N-dimethylamino-phenyl)-indan-1-one (MC-2-37) $^1$H-NMR (CDCl$_3$): δ 2.07 (s, 3H, NHCOCH$_3$), 2.70 (m, J=6.0 Hz, 2H, CH$_2$), 3.05 (s, 6H, 2×CH$_3$), 3.16 (t, J=6.3 Hz, 2H, CH$_2$), 6.91 (brs, 2H, ArH), 7.24 (d, J=8.7 Hz, 2H, ArH), 7.56 (s, 1H, ArH), 7.60 (s, 1H, ArH), 8.56 (s, 1H, ArH).

i) 5-N-Acetamido-6-(2'-furano)-indan-1-one (MC-2-11) $^1$H-NMR (CDCl$_3$): δ 2.24 (s, 3H, NHCOCH$_3$), 2.70 (m, J=6.6 Hz, 2H, CH$_2$), 3.15 (t, J=6.6 Hz, 2H, CH$_2$), 6.58 (dd, J=2.1, 3.3 Hz, 1H, ArH), 6.69 (d, J=0.9 Hz, 1H, ArH), 7.59 (dd, J=0.9, 2.1 Hz, 1H, ArH), 7.89 (s, 1H, ArH), 8.60 (s, 1H, ArH) 8.86 (s, 1H, ArH); $^{13}$C-NMR (CDCl$_3$): δ 25.1, 25.6, 36.3, 108.8, 111.8, 118.0, 119.4, 122.7, 132.5, 139.8, 142.4, 151.4, 155.8, 168.4, 205.3; GCMS: R$_t$=19.8 min., M$^+$=255 m/z.

j) 5-N-Acetamido-6-(3'-thiopheno)-indan-1-one (MC-2-31) $^1$H-NMR (CDCl$_3$): δ 2.10 (s, 3H, NHCOCH$_3$), 2.69 (m, J=6.0 Hz, 2H, CH$_2$), 3.14 (t, J=6.0 Hz, 2H, CH$_2$), 7.13 (dd, J=1.2, 5.1 Hz, 1H, ArH), 7.34 (dd, J=1.2, 3.0 Hz, 1H, ArH), 7.52 (dd, J=2.7, 4.8 Hz, 1H, ArH), 7.61 (brs, 1H, ArH), 7.63 (s, 1H, ArH), 8.53 (s, 1H, ArH). GCMS: R$_t$=15.4 min., M$^+$=271 m/z.

NMR Data for N-(2-Amino-5-(4'-methoxyphenyl)-8H-indeno[1,2-d]thiazol-6-yl)-acetamide Hydroiodides (FIG. 13)

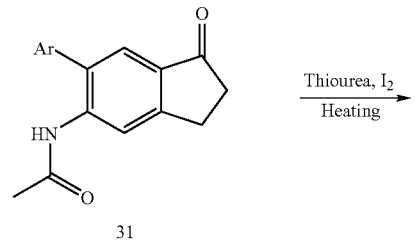

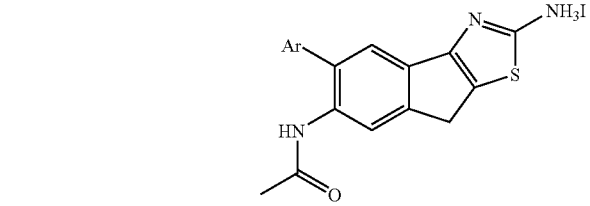

Ar = substituted aromatic and heteroaomatic substituent

Procedure: A mixture of ketone (1.0 mmol), thiourea (2.5 mmol), and iodine (1.1 mmol) in dry ethanol (~2 mL) was heated with stirring on an oil bath at 90-100° C. After cooling to room temperature the residue triturated 3-4 times with ether (~5 mL each), once with hot water. Upon cooling to room temperature solid product were filtered off, the solid then dried in open atmosphere and then under vacuo. Yields 70-90%.

a) N-(2-Amino-5-(4'-methoxy-phenyl)-8H-indeno[1,2-d]thiazol-6-yl)-acetamide hydroiodide (MC-2-34) $^1$H-NMR (DMSO-d$_6$): δ 1.90 (s, 3H, CH$_3$), 3.79 (s, 3H, CH$_3$), 3.81 (s, 2H, CH$_2$), 7.02 (d, J=8.4 Hz, 2H, ArH), 7.32 (d, J=8.4 Hz, 2H, ArH), 7.46 (s, 1H, ArH), 7.62 (brs, 1H, ArH), 9.24 (s, 1H, NH).

b) N-(2-Amino-5-(3',4'-dimethoxy-phenyl)-8H-indeno[1,2-d]thiazol-6-yl)-acetamide hydroiodide (MC-2-15) $^1$H-NMR (DMSO-d$_6$): δ 1.91 (s, 3H, CH$_3$), 3.75 (s, 3H, CH$_3$), 3.79 (brs, 5H, CH$_3$+CH$_2$), 6.91 (dd, J=1.8, 8.1 Hz, 1H, ArH), 6.95 (d, J=1.8 Hz, 1H, ArH), 7.04 (d, J=8.4 Hz, 1H, ArH), 7.44 (brs, 1H, ArH), 7.63 (brs, 1H, ArH), 9.23 (s, 1H, NH).

c) N-2-Amino-5-(3',4'-methylenedioxy-phenyl)-8H-indeno[1,2-d]thiazol-6-yl)-acetamide hydroiodide (MC-2-61) $^1$H-NMR (DMSO-d$_6$): δ 1.89 (s, 3H, CH$_3$), 3.76 (s, 3H, CH$_2$), 6.05 (s, 2H, CH$_2$), 6.82 (d, J=8.1 Hz, 1H, ArH), 6.84 (brs, 1H, ArH), 6.99 (d, J=8.1 Hz, 1H, ArH), 7.35 (brs, 1H, ArH), 7.58 (brs, 1H, ArH), 9.22 (s, 1H, NH).

d) N-(2-Amino-5-(4'-phenoxy-phenyl)-8H-indeno[1,2-d]thiazol-6-yl)-acetamide hydroiodide (MC-2-25) $^1$H-NMR (DMSO-d$_6$): δ 1.90 (s, 3H, CH$_3$), 3.81 (s, 2H, CH$_2$), 7.07 (m, 4H, ArH), 7.17 (t, J=7.5 Hz, 1H, ArH), 7.40 (m, 4H, ArH), 7.47 (s, 1H, ArH), 7.63 (brs, 1H, ArH), 9.31 (s, 1H, NH).

e) N-(2-Amino-5-(3'-nitro-phenyl)-8H-indeno[1,2-d]thiazol-6-yl)-acetamide hydroiodide (MC-2-35) $^1$H-NMR (DMSO-d$_6$): δ 1.86 (s, 3H, CH$_3$), 3.85 (s, 3H, CH$_3$), 7.65 (s, 1H, ArH), 7.64 (s, 1H, ArH), 7.75 (t, J=7.8 Hz, 1H, ArH), 7.84 (d, J=71.8 Hz, 1H, ArH), 8.19 (s, 1H, ArH), 8.25 (dd, J=2.4, 7.8, 1H, ArH), 9.54 (s, 1H, ArH).

f) N-(2-Amino-5-(3'-hydroxymethyl-phenyl)-8H-indeno[1,2-d]thiazol-6-yl)-acetamide hydroiodide (MC-2-62) $^1$H-NMR (DMSO-d$_6$): δ 1.90 (s, 3H, CH$_3$), 3.80 (s, 2H, CH$_2$), 4.51 (s, 2H, CH$_2$), 7.35-7.50 (m, 3H, ArH), 7.60 (s, 1H, ArH), 8.96 (brs, 1H, NH), 9.14 (brs, 1H, NH), 9.32 (s, 1H, ArH).

g) N-(2-Amino-5-bromo-8H-indeno[1,2-d]thiazol-6-yl)-acetamide hydroiodide (MC-2-217) $^1$H-NMR (DMSO-d$_6$): δ 2.07 (s, 3H, COCH$_3$), 3.75 (s, 2H, CH$_2$), 7.71 (s, 2H, ArH), 9.50 (s, 1H, NH).

Generation of Free Aminothiazoles from Iodide Salts

A solution of iodide salt (1 mmol) in hot water was adjusted to pH>10 with 35% ammonia and extracted twice with 10 mL ethyl acetate. The organic layers were combined, washed with brine, dried and evaporated.

General Procedure for the Bromination of Hydroxy-indanones and -tetralones (FIG. 8):

The starting compound (10 mmol) was dissolved in glacial acetic acid (50 mL) and sodium acetate, to it was added dropwise a solution of bromine (10.5 mmol) in glacial acetic acid (5 mL) over period of 1 hr. The progress of reaction was monitored by TLC analysis usually a non-polar bromo compound was formed. The reaction mixture was then concentrated to ¼ volume by distilling off the acetic acid. The mixture was then diluted with ether (~50 mL), washed with water (2×50 mL), dil. Na$_2$CO$_3$ carefully and finally with brine. The organic layer separated dried over Na$_2$SO$_4$ and evaporated to isolate the mixture of mono-brominated and di-brominated compounds (~3:1 respectively). Purification of mixture by column chromatography over silica gel afforded mono-brominated compound. Yields 55-60%.

a) 4-Bromo-5-hydroxy-indan-1-one: (MC-2-90) $^1$H-NMR (CDCl$_3$): δ 2.72 (m, 2H, CH$_2$), 3.02 (t, J=6.3 Hz, 2H, CH$_2$), 6.17 (s, 1H, OH), 7.05 (d, J=8.1 Hz, 1H, ArH), 7.65 (d, J=8.1 Hz, 1H, ArH); GCMS: R$_t$=15.1 min., M$^+$=226/228 (1:1) m/z.

b) 5-Bromo-6-hydroxy-tetral-1-one: (MC-2-92) $^1$H-NMR (CDCl$_3$): δ 2.14 (m, 2H, CH$_2$), 2.61 (t, J=6.0 Hz, 2H), 2.99 (t, J=6.3 Hz, 2H, CH$_2$), 6.07 (s, 1H, OH), 7.00 (d, J=8.4 Hz, 1H, ArH), 8.01 (d, J=8.1 Hz, 1H, ArH); GCMS: R$_t$=15.8 min., M$^+$=240/242 (1:1) m/z.

General Procedure for the Iodination of Hydroxy-indan-1-ones and Hydroxy-tetral-1-ones (FIG. 8):

The starting material (10 mmol) was dissolved in methanol (50 mL) and to this solution ammonia (10 mL, 30% v/v) was added. Iodine solution in methanol (10 mol, ~10 mL) was added drop wise to the above solution. The mixture was stirred at room temperature for additional 30 minutes. The progress of reaction was monitored by TLC analysis. The solvents were removed under reduced pressure and the residue was diluted with ethyl acetate (~50 mL). The ethyl acetate layer was then washed with dil. Sodium thiosulfate solution, water and finally with brine. Drying over Na$_2$SO$_4$ followed by evaporation led to isolation of crude material. Purification over silica gel afforded mono-iodinated compound. Yields 55-65%.

a) 5-Hydroxy-4-iodo-indan-1one: (MC-2-33) $^1$H-NMR (CDCl$_3$): δ 2.74 (m, 2H, CH$_2$), 2.96 (t, J=5.7 Hz, 2H, CH$_2$), 6.13 (s, 1H, OH), 7.01 (d, J=8.1 Hz, 1H, ArH), 7.65 (d, J=8.1 Hz, 1H, ArH).

b) 5-Hydroxy-6-iodo-tetral-1-one: (MC-2-40) $^1$H-NMR (CDCl$_3$): δ 2.14 (m, 2H, CH$_2$), 2.64 (t, J=6.3 Hz, 2H, CH$_2$), 2.96 (t, J=6.3 Hz, 2H, CH$_2$), 5.46 (s, 1H, OH), 7.38 (d, J=8.1 Hz, 1H, ArH), 7.63 (d, J=8.1 Hz, 1H, ArH); GCMS: R$_t$=14.9 min., M$^+$=288 m/z.

Figure 8:
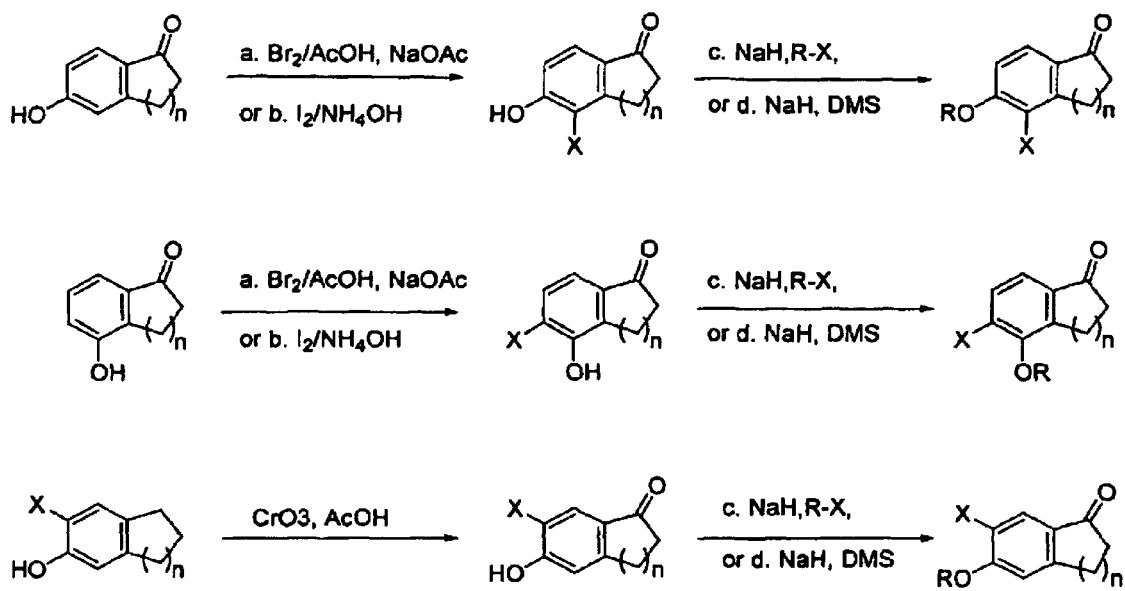

General Procedure for Methylation of Hydroxy-indanones and Tetralones (FIG. 8)

The hydroxy-indan-1-one or -tetral-1-one (5 mmol) was dissolved in THF (25 mL). To the solution dimethyl sulfate (6 mmol) followed by sodium hydride (6 mmol) were added. The mixture was refluxed for 3-4 hrs. After cooling the reaction mixture to room temperature solvents were evaporated under reduced pressure and the residue was diluted with ether (~30 mL). The ethereal layer was washed successively with dil. HCl followed by dil. Na$_2$CO$_3$ and finally with brine. The organic layer dried and concentrated to yield oily residue. Purification of residue over silica gel afforded the methyl ethers. (Yields 85-95%).

a) 4-Bromo-5-methoxy-indan-1-one: (MC-2-93-2) $^1$H-NMR (CDCl$_3$): δ 2.70 (m, 2H, CH$_2$), 3.05 (t, J=6.3 Hz, 2H, CH$_2$), 3.99 (s, 3, CH$_3$), 6.94 (d, J=8.1 Hz, 1H, ArH), 7.71 (d, J=8.1 Hz, 1H, ArH); GCMS: R$_t$=15.9 min., M$^+$=240/242 (1:1) m/z.

b) 4-Iodo-5-methoxy-indan-1-one: (MC-2-59) $^1$H-NMR (CDCl$_3$): δ 2.66 (m, 2H, CH$_2$), 2.92 (t, J=6.6 Hz, 2H, CH$_2$), 3.96 (s, 3, OMe), 6.81 (d, J=8.4 Hz, 1H, ArH), 7.67 (d, J=8.4 Hz, 1H, ArH); $^{13}$C-NMR (CDCl$_3$): δ 31.2, 36.5, 56.8, 86.5, 110.2, 125.1, 132.0, 161.1, 163.0, 205.1; GCMS: R$_t$=15.4 min., M$^+$=288 c) 5-Bromo-6-methoxy-tetral-1-one: (MC-2-94-2) $^1$H-NMR (CDCl$_3$): δ 2.12 (m, 2H, CH$_2$), 2.60 (t, J=6.6 Hz, 2H), 3.02 (t, J=6.3 Hz, 2H, CH2), 3.96 (s, 3H, OMe), 6.87 (d, J=8.7 Hz, 1H, ArH), 8.06 (d, J=8.7 Hz, 1H, ArH); GCMS: $R_t$=16.9 min., $M^+$=254/256 (1:1) m/z.

d) 6-Iodo-5-methoxy-tetral-1-one: (MC-2-60) $^1$H-NMR (CDCl$_3$): δ 2.14 (m, 2H, CH$_2$), 2.63 (t, J=5.7 Hz, 2H), 3.01 (t, J=5.7 Hz, 2H, CH$_2$), 3.80 (s, 3H, OMe), 7.54 (d, J=8.1 Hz, 1H, ArH), 7.76 (d, J=8.1 Hz, 1H, ArH); $^{13}$C-NMR (CDCl$_3$): δ 22.6, 241., 38.4, 60.3, 99.3, 124.2, 134.3, 137.1, 138.0, 157.2, 197.3 GCMS: $R_t$=15.2 min., $M^+$=302 m/z.

Figure 9:
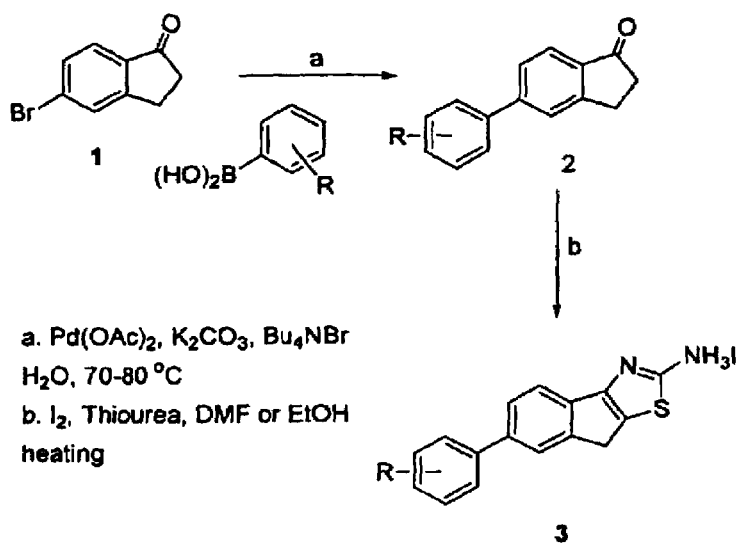

General Procedure for the Modified Suzuki Coupling of 5-bromo-indanone and Aryl Boronic Acids Compounds 2a-x (FIG. 9)

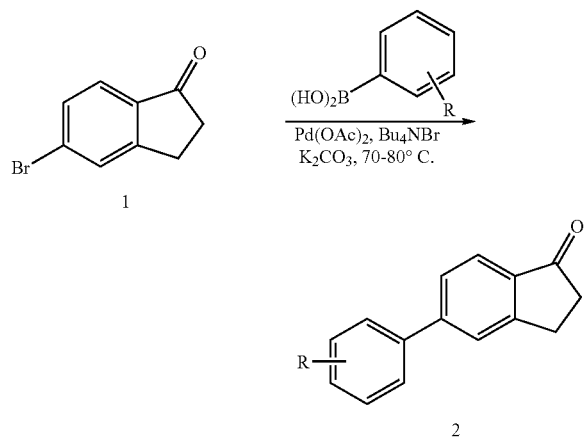

The non-homogenous solution of 5-bromo-indanone (1.0 mmol), aryl boronic acid (1.1 mmol), tetrabutyl ammonium bromide (1.0 mmol) and K$_2$CO$_3$ (5.0 mmol) in deionised and thoroughly deoxygenated water (2.0 mL) was purged with N$_2$ for 30 minutes and then Pd(OAc)$_2$ (0.05 mmol) was added. The mixture was heated on oil bath with vigorous stirring at 70-80° C. for 2-3 hrs. The progress of reaction was followed by TLC analysis and in all most all cases more polar biaryl product formation was observed. At the end of the heating, reaction was allowed to cool down to room temperature, diluted with water (10 mL) and extracted with either ethylacetate or methylene chloride (2×15 mL). The combined organic layer was washed with water and finally with brine. The drying over Na$_2$SO$_4$ followed by concentration on rotary evaporator under reduced pressure afforded crude material. Purification of crude material by column chromatography over silica gel using hexanes:ethyl acetate gradient with increased polarity yielded pure biaryl-indanones as solids. Yields (70-89%).

a) 5-Phenyl-indan-1-one: Characterization data in agreement with reported data. Ref: J. Med. Chem. 1999, 431-436; Bioorg. Med. Chem. 2000, 1245-1252 (MC-2-246)

b) 5-(1-Naphthyl)-indan-1-one (MC-2-105) $^1$H-NMR (CDCl$_3$): δ 2.78 (m, 2H, CH$_2$), 3.24 (t, J=5.7 Hz, 2H, CH$_2$), 7.42-7.56 (m, 5H, ArH), 7.60 (brs, 1H, ArH), 7.82-7.95 (m, 4H, ArH). $^{13}$C-NMR (CDCl$_3$): δ 25.6, 36.2, 123.0, 124.9, 125.1, 125.6, 126.0, 126.6, 127.8, 129.1, 130.7, 133.3, 135.6, 138.7, 147.0, 154.9, 206.0 c) 5-(2-Naphthyl)-indan-1-one (MC-2-104) $^1$H-NMR (CDCl$_3$): δ 2.77 (m, 2H, CH$_2$), 3.24 (t, J=6.6 Hz, 2H, CH$_2$), 7.50-7.65 (m, 2H, ArH), 7.60-7.80 (m, 2H, ArH), 7.81 (d, J=0.6 Hz, 1H, ArH), 7.85-7.94 (m, 3H, ArH), 7.96 (d, J=8.4 Hz, 1H, ArH), 8.10 (d, J=1.5 Hz, 1H, ArH). $^{13}$C-NMR (CDCl$_3$): δ 25.9, 36.5, 123.9, 125.1, 126.4, 126.8, 127.5, 128.2, 128.5, 132.8, 133.3, 135.8, 137.2, 147.3, 155.7, 206.4 d) 5-4'-Methoxy-phenyl)-indan-1-one: Characterization data in agreement with reported data.

Ref: Bioorg. Med. Chem. 2000, 1245-1252; Bull. Chem. Soc. Fr. 1968, 2111-2117 (MC-2-256)

e) 5-(3'-Methoxy-phenyl)-indan-1-one: Characterization data in agreement with reported data Ref: Bioorg. Med. Chem. Lett. 1999, 431-436 (MC-1-267)

f) 5-(2'-Methoxy-phenyl)-indan-1-one (MC-1-268) $^1$H-NMR (CDCl$_3$): δ 2.73 (m, J=6.6 Hz, 2H, CH$_2$), 3.19 (t, J=6.6 Hz, 2H, CH$_2$), 3.83 (s, 3H, OCH$_3$), 7.02 (d, J=8.4 Hz, 1H, ArH), 7.07 (dd, J=1.2, 7.5 Hz, 1H, ArH), 7.31-7.41 (m, 2H, ArH), 7.54 (dd, J=1.8, 8.1 Hz, 1H, ArH), 7.61 (brs, 1H, ArH), 7.79 (d, J=8.1 Hz, 1H, ArH). $^{13}$C-NMR (CDCl$_3$): δ 25.8, 36.4, 55.5, 111.2, 120.8, 123.1, 127.5, 129.1, 129.5, 129.6, 130.7, 135.6, 145.3, 155.0, 156.3, 206.7; GCMS: $R_t$=12.5 min., $M^+$=188 m/z.

g) 5-(4'-Phenoxy-phenyl)-indan-1-one (MC-1-281) $^1$H-NMR (CDCl$_3$): δ 2.73 (m, J=6.6 Hz, 2H, CH$_2$), 3.19 (t, J=6.6 Hz, 2H, CH$_2$), 7.06-7.13 (m, 4H, ArH), 7.16 (d, J=8.7 Hz, 1H, ArH), 7.35-7.41 (m, 2H, ArH), 7.56-7.63 (m, 3H, ArH), 7.65 (brs, 1H, ArH), 7.81 (d, J=8.1 Hz, 1H, ArH); GCMS: $R_t$=27.5 min., $M^+$=300 m/z.

h) 5-(3'-Nitro-phenyl)-indan-1-one (MC-1-278) $^1$H-NMR (CDCl$_3$): δ 2.77 (m, J=6.0 Hz, 2H, CH$_2$), 3.24 (t, J=6.0 Hz, 2H, CH$_2$), 7.63 (ddd, J=4H, ArH), 7.68 (d, J=8.1 Hz, 1H, ArH), 7.731 (d, J=0.6 Hz, 1H, ArH), 7.87 (d, J=8.1 Hz, 1H, ArH), 7.96 (ddd, J=1.2, 1.8, 7.5 Hz, 1H, ArH) 8.27 (ddd, J=1.2, 3.6, 8.1 Hz, 1H, ArH), 8.49 (t, J=1.8 Hz, 1H, ArH); $^{13}$C-NMR (CDCl$_3$): δ 25.8, 36.4, 122.3, 122.9, 124.4, 125.4, 126.7, 129.9, 133.3, 136.9, 141.9, 144.8, 148.7, 155.9, 206.2; GCMS: $R_t$=20.8 min., $M^+$=253 m/z.

i) 5-(3'-Amino-phenyl)-indan-1-one (MC-1-283) $^1$H-NMR (CDCl$_3$): δ 2.73 (m, J=6.6 Hz, 2H, CH$_2$), 3.18 (t, J=6.3 Hz, 2H, CH$_2$), 6.73 (ddd, J=0.9, 2.4, 8.1 Hz, 1H, ArH), 6.93 (t, J=1.8 Hz, 1H, ArH), 7.01 (ddd, J=0.9, 1.8, 7.8 Hz, 1H, ArH), 7.26 (t, J=8.4, 1H, ArH), 7.5d (dd, J=1.5, 8.1 Hz, 1H, ArH), 7.64 (brs, 1H, ArH), 7.79 (d, J=7.8 Hz, 1H, ArH). $^{13}$C-NMR (CDCl$_3$): δ 25.8, 36.5, 114.0, 115.0, 117.8, 123.9, 125.0, 126.7, 129.8, 135.9, 141.3, 146.8, 147.9, 155.7, 206.6; GCMS: $R_t$=19.6 min., $M^+$=223 m/z.

j) 5-(4'-N,N-Dimethylamino-phenyl)-indan-1-one (MC-1-282) $^1$H-NMR (CDCl$_3$): δ 2.71 (m, J=6.6 Hz, 2H, CH$_2$), 3.02 (s, 6H, N—CH$_{3\times2}$) 3.16 (t, J=6.3 Hz, 2H, CH$_2$), 6.81 (d, J=8.4 Hz, 2H, ArH), 7.55 (dd, J=1.8, 7.8 Hz, 1H, ArH), 7.57 (d, J=8.4 Hz, 2H, ArH), 7.63 (dd, J=0.6, 8.1 1H, ArH), 7.77 (d, J=8.1 Hz, 1H, ArH). $^{13}$C-NMR (CDCl$_3$): δ 25.8, 36.5, 114.0, 115.0, 117.8, 123.9, 125.0, 126.7, 129.8, 135.9, 141.3, 146.8, 147.9, 155.7, 206.6; GCMS: $R_t$=19.6 min., $M^+$=223 m/z.

k) 5-(3',4'-Dimethoxy-phenyl)-indan-1-one (MC-1-279) $^1$H-NMR (CDCl$_3$): δ 2.73 (m, J=6.0 Hz, 2H, CH$_2$), 3.19 (t, J=6.6 Hz, 2H, CH$_2$), 3.94 (s, 3H, OCH$_3$), 3.97 (s, 3H, OCH$_3$), 6.97 (d, J=8.4 Hz, 1H, ArH), 7.14 (d, J=2.1 Hz, 1H, ArH), 7.21 (dd, J=2.1, 8.4 Hz, 1H, ArH), 7.57 (brd, J=7.8 Hz, 1H, ArH), 7.64 (d, J=0.6 Hz, 1H, ArH), 7.80 (d, J=7.8 Hz, 1H, ArH). GCMS: $R_t$=20.9 min., $M^+$=268 m/z.

l) 5-(2',4'-Dimethoxy-phenyl)-indan-1-one (MC-2-176) $^1$H-NMR (CDCl$_3$): δ 2.71 (m, J=6.0 Hz, 2H, CH$_2$), 3.17 (t, J=6.0 Hz, 2H, CH$_2$), 3.81 (s, 3H, OCH$_3$), 3.86 (s, 3H, OCH$_3$), 6.57 (brs, 1H, ArH), 6.59 (dd, J=2.4, 7.5 Hz, 7.26 (d, J=7.4 Hz, 1H, ArH), 7.51 (dd, J=1.5, 7.8 Hz, 1H, ArH), 7.58 (brs, 1H, ArH), 7.76 (d, J=8.1 Hz, 1H, ArH); $^{13}$C-NMR (CDCl$_3$): δ 25.7, 36.4, 55.4, 55.5, 98.9, 104.7, 122.4, 123.0, 127.2, 128.9, 131.3, 135.1, 145.1, 155.1, 157.4, 160.6, 206.7; GCMS: $R_t$=24.8 min., $M^+$=268 m/z.

m) 5-(3',4'-Methlyenedioxy-phenyl)-indan-1-one (MC-1-277) $^1$H-NMR (CDCl$_3$): δ 2.73 (m, J=6.6 Hz, 2H, CH$_2$), 3.18 (t, J=6.0 Hz, 2H, CH$_2$), 6.02 (s, 2H, OCH$_2$O), 6.90 (dd, J=1.5, 7.5 Hz, 1H, ArH), 7.10 (brs, 1H, ArH), 7.12 (dd, J=1.8, 7.8 Hz, 1H, ArH), 7.52 (brd, J=8.1 Hz, 1H, ArH), 7.59 (brs, 1H, ArH), 7.78 (d, J=8.1 Hz, 1H, ArH). $^{13}$C-NMR (CDCl$_3$): δ 25.8, 36.4, 55.5, 101.3, 107.7, 108.7, 121.2, 124.0, 124.6, 126.4, 134.4, 135.6, 147.3, 147.9, 148.3, 155.8, 206.4; GCMS: R$_t$=20.1 min., M$^+$=252 m/z.

n) 5-(2'-Benzofurano)-indan-1-one (MC-1-280) $^1$H-NMR (CDCl$_3$): δ 2.74 (m, J=6.6 Hz, 2H, CH$_2$), 3.18 (t, J=6.0 Hz, 2H, CH$_2$), 7.18 (s, 1H, ArH), 7.23-7.29 (m, 2H, ArH), 7.34 (dt, J=1.5, 8.4 Hz, 1H, ArH), 7.54 (brd, J=8.4 Hz, 1H, ArH), 7.62 (brd, J=7.8 Hz, 1H, ArH), 7.83 (ABd, J=8.1 Hz, 2H, ArH), 7.98 (s, 1H, ArH).

o) 5-(3',4'-Dichloro-phenyl)-indan-1-one (MC-2-49) $^1$H-NMR (CDCl$_3$): δ 2.75 (m, J=6.0 Hz, 2H, CH$_2$), 3.21 (t, J=6.3 Hz, 2H, CH$_2$), 7.45 (dd, J=2.4, 8.4, 1H, ArH), 7.54, (d, J=8.1 Hz, 1H, ArH), 7.63 (d, J=0.9 Hz, 1H, ArH), 7.72 (d, J=2.4 Hz, 1H, ArH), 7.83 (d, J=8.1 Hz, 1H, ArH); $^{13}$C-NMR (CDCl$_3$): δ 25.8, 36.4, 124.3, 125.0, 126.4, 126.6, 129.2, 130.8, 132.5, 133.1, 136.6, 140.1, 144.9, 155.8, 206.3; GCMS: R$_t$=20.26 min., M$^+$=276 m/z.

p) 5-(3',5'-Dichloro-phenyl)-indan-1-one (MC-2-50) $^1$H-NMR (CDCl$_3$): δ 2.75 (m, J=6.0 Hz, 2H, CH$_2$), 3.21 (t, J=6.3 Hz, 2H, CH$_2$), 7.40 (dd, J=1.8, 2.1 Hz, 1H, ArH), 7.50, (m, 2H, ArH), 7.55 (d, J=8.1 Hz, 1H, ArH), 7.64 (d, J=0.6 Hz, 1H, ArH), 7.83 (d, J=8.1 Hz, 1H, ArH); $^{13}$C-NMR (CDCl$_3$): δ 23.7, 36.3, 124.2, 125.1, 125.8, 126.5, 128.0, 135.4, 143.0, 144.5, 155.7, 206.7; GCMS: R$_t$=19.32 min., M$^+$=276 m/z.

q) 5-(3',4',5'-Trimethoxy-phenyl)-indan-1-one (MC-2-103) $^1$H-NMR (CDCl$_3$): δ 2.75 (m, J=6.0 Hz, 2H, CH$_2$), 3.21 (t, J=6.3 Hz, 2H, CH$_2$), 3.91 (s, 3H, OMe), 3.94 (s, 6H, OMe ×2), 6.81 (s, 2H, ArH), 7.57 (d, J=8.7 Hz, 1H, ArH), 7.63 (brs, 1H, ArH), 7.81 (d, J=8.4 Hz, 1H, ArH); $^{13}$C-NMR (CDCl$_3$): δ 25.8, 36.4, 56.1, 60.8, 104.5, 123.7, 124.8, 126.4, 135.6, 135.7, 138.1, 147.4, 153.3, 155.6, 206.1.

r) 5-(2',3',4'-Trimethoxy-phenyl)-indan-1-one (MC-2-177) $^1$H-NMR (CDCl$_3$): δ 2.71 (m, J=6.0 Hz, 2H, CH$_2$), 3.17 (t, J=5.7 Hz, 2H, CH$_2$), 3.68 (s, 3H, OMe), 3.90 (s, 3H, OMe), 3.92 (s, 6H, OMe), 6.75 (d, J=8.4 Hz, 1H, ArH), 7.05 (d, J=8.7 Hz, 1H, ArH), 7.50 (dd, J=1.2, 8.4 Hz, 1H, ArH), 7.59 (brs, 1H, ArH), 7.76 (d, J=7.8 Hz, 1H, ArH); $^{13}$C-NMR (CDCl$_3$): δ 25.6, 36.2, 55.8, 60.8, 60.9, 107.3, 123.0, 124.7, 126.9, 128.4, 135.2, 142.3, 144.7151.2, 153.6, 155.0, 206.5; R$_t$=25.7 min., M$^+$=298 m/z.

s) 5-(3'-hydroxymethyl-phenyl)-indan-1-one (MC-2-190) $^1$H-NMR (CDCl$_3$): δ 2.74 (m, J=6.3 Hz, 2H, CH$_2$), 3.20 (t, J=6.3 Hz, 2H, CH$_2$), 4.77 (s, 2H OCH$_2$), 7.48 (d, J=9.0 Hz, 2H, ArH), 7.58 (m, 2H, ArH), 7.66 (d, J=9.0 Hz, 2H, ArH), 7.82 (d, J=7.8 Hz, 1H, Ar); $^{13}$C-NMR (CDCl$_3$): δ 25.7, 36.3, 64.8, 123.9, 124.9, 125.8, 126.4, 126.5, 126.7, 128.9, 135.7, 140.1, 141.8, 147.3, 155.8, 206.9; GCMS: R$_t$=14.9 min., M$^-$=238 m/z.

t) 5-(4'-hydroxymethyl-phenyl)-indan-1-one (MC-2-191) $^1$H-NMR (CDCl$_3$): δ 2.71 (m, J=6.0 Hz, 2H, CH$_2$), 3.20 (t, J=5.7 Hz, 2H, CH$_2$), 4.79 (s, 2H OCH$_2$), 7.41 (bd, J=7.5 Hz, 1H, ArH), 7.47 (t, J=7.5 Hz, 1H, ArH), 7.54-7.63 (m, 2H, ArH), 7.65 (brs, 1H, ArH), 7.69 (s, 1H, ArH), 7.82 (d, J=8.1 Hz, 1H, Ar); $^{13}$C-NMR (CDCl$_3$): δ 25.8, 36.5, 64.9, 124.1, 125.0, 126.3, 127.5, 127.6, 135.9, 139.5, 141.0, 146.2, 155.8, 206.6; GCMS: R$_t$=14.9 min., M$^+$=238 m/z.

u) 5-(2'-Furano)-indan-1-one (MC-1-263) $^1$H-NMR (CDCl$_3$): δ 2.72 (m, J=6.6 Hz, 2H, CH$_2$), 3.16 (t, J=6.6 Hz, 2H, CH$_2$) 6.53 (dd, J=2.1, 3.6 Hz, 1H, ArH), 6.83 (d, J=3.3 Hz, 1H, ArH), 7.54 (d, J=1.5 Hz, 1H, ArH), 7.67 (d, J=8.1, Hz, 1H, ArH), 7.76 (d, J=7.5 Hz, 1H, ArH), 7.77 (brs, 1H, ArH). GCMS: R$_t$=16.7 min., M$^+$=198 m/z.

v) 5-(3'-Furano)-indan-1-one (MC-2-184) $^1$H-NMR (CDCl$_3$): δ 2.71 (m, J=6.6 Hz, 2H, CH$_2$), 3.16 (t, J=5.4 Hz, 2H, CH$_2$) 6.75 (dd, J=0.9, 2.1 Hz, 1H, ArH), 7.50 (brd, J=7.8 Hz, 1H, ArH), 7.51 (d, J=1.5 Hz, 1H, ArH), 7.57 (brs, 1H, ArH), 7.76 (d, J=7.8 Hz, 1H, ArH), 7.84 (dd, J=0.9, 1.8 Hz, 1H, ArH); $^{13}$C-NMR (CDCl$_3$): δ 25.6, 36.3, 108.6, 123.2, 124.1, 125.0, 125.7, 135.6, 138.7, 139.7, 144.1, 155.9, 206.2; GCMS: R$_t$=16.7 min., M$^+$=198 m/z.

w) 5-(2'-Thiopheno)-indan-1-one (MC-1-261) $^1$H-NMR (CDCl$_3$): δ 2.72 (m, J=6.6 Hz, 2H, CH$_2$), 3.17 (t, J=6.6 Hz, 2H, CH$_2$) 7.12 (dd, J=3.6, 5.1 Hz, 1H, ArH), 7.38 (dd, J=0.9, 5.1 Hz, 1H, ArH), 7.45 (dd, J=0.9, 3.6 Hz, 1H, ArH), 7.63 (dd, J=1.5, 8.17 Hz, 1H, ArH), 7.69 (m, 1H, ArH), 7.75 (d, J=8.1 Hz, 1H, ArH). GCMS: R$_t$=16.7 min., M$^+$=214 m/z.

x) 5-(3'-Thiopheno)-indan-1-one (MC-2-183) $^1$H-NMR (CDCl$_3$): δ 2.73 (m, J=6.6 Hz, 2H, CH$_2$), 3.18 (t, J=5.7 Hz, 2H, CH$_2$) 7.44 (brd, J=2.1 Hz, 2H, ArH), 7.59 (t, J=2.1 Hz, 1H, ArH), 7.61 (d, J=8.1, 1H, ArH), 7.68 (brs, 1H, ArH), 7.78 (d, J=8.1 Hz, 1H, ArH); $^{13}$C-NMR (CDCl$_3$): δ 25.7, 36.4, 122.3, 124.0, 124.1, 125.8, 126.2, 126.7, 135.7, 141.2, 141.7, 155.9, 206.3; GCMS: R$_t$=18.6 min., M$^+$=214 m/z.

Preparation of Aryl and Heteroaryl-substituted Compounds

The procedure for preparing aryl and heteroaryl-substituted compounds of the present invention generally includes preparing biaryl indanones via palladium-catalyzed Suzuki coupling, followed by conversion to the corresponding aminothiazoles as described below. The aryl and heteroaryl substituents may be found at the R$^1$, R$^2$, R$^3$ and R$^4$ positions.

General Procedure for the Synthesis of Biaryl Indanones Using Palladium Catalyzed Suzuki Coupling 5-Bromoindan-1-one (2.0 mmol), tetrabutyl ammonium bromide (2.2 mmol), K$_2$CO$_3$ (5.0 mmol) and aryl boronic acids (2.1 mmol) were suspended in thoroughly deoxygenated H$_2$O (3.0 mL). The suspension was stirred vigorously under nitrogen atmosphere for 10 minutes and then Pd(II) acetate (1.0 mg) was added and the mixture was heated on an oil bath at 70° C. for 2 to 3 hours. After cooling the reaction mixture to room temperature, ethyl acetate (~20 mL) was added and extracted. The aqueous layer was further extracted with ethyl acetate (~20 mL). The combined organic layer was washed with brine and dried over Na$_2$SO$_4$ and concentrated under reduced pressure to yield crude product. Further purification by column chromatography over silica gel yielded pure products in yields of from 65 to 90%.

Synthesis of Variety of Aromatic Ketones

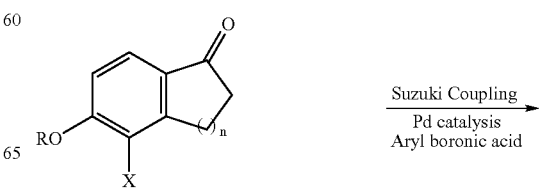

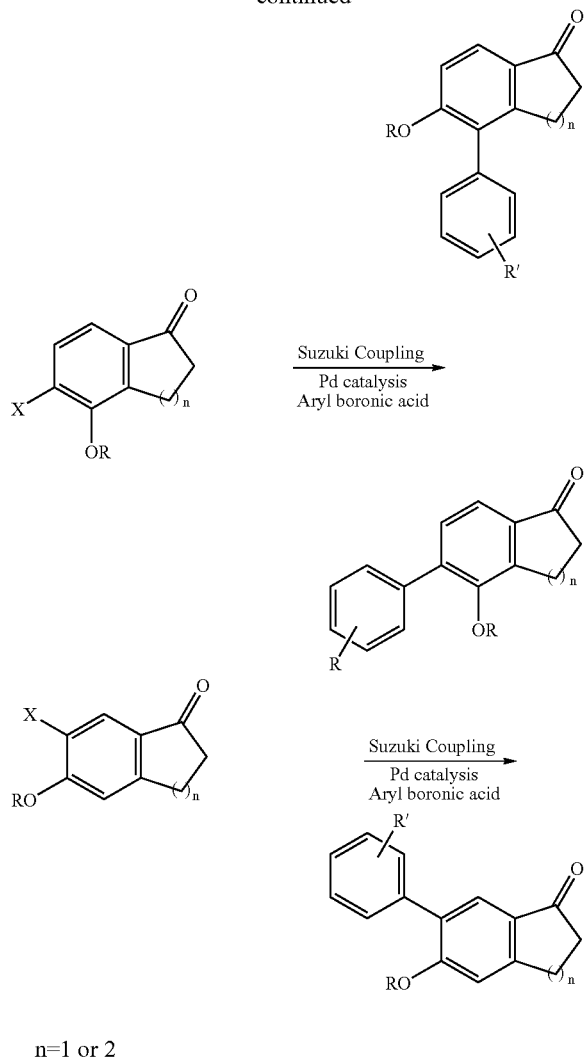

n=1 or 2
R=Alkyl, allyl, and other subsituents
R'=Alkoxy, alkyl, aryloxy, amino, halo, nitro or combination of thereof etc.

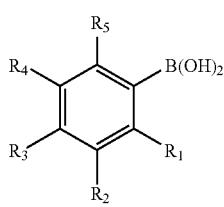

Aryl boronic acids =

Angiogenic Activity

Adenosine stimulates angiogenesis in the CAM assay. Work done in the CAM by previous investigators has yielded conflicting results with respect to adenosine as a stimulator of angiogenesis. Our approach was to see if adenosine would stimulate angiogenesis in the windowed CAM model.

Fertile White Leghorn chicken eggs were obtained from Truslow Farms (Chesterfield, Mo.). Eggs were incubated at 37° for 7 days, then a 1.5 cm window was cut into each egg over the CAM. Pellets were applied to the CAMS and the windows closed with cellophane tape. Eggs were incubated until day 14 when the CAMS were fixed. Adenosine was applied to the CAM via Elvdx pellets as described by Dusseau (Dusseau et al., *Stimulation of Angiogenesis by Adenosine on the Chick Chorioallantoic Membrane, Circ. Res.*, 59, 163-170, 1986). Each pellet had a 10 ul volume and contained 3 mg adenosine powder. Control pellets did not contain adenosine powder, only the Elvax polymer. The pellets were placed on the CAM where there were a few vessels present and were left in place for seven days. The CAMS then were fixed in 10% buffered formalin and vessels were counted under 20× magnification using a Nikon stereomicroscope. The quantitation of vascular number is presented as vascular density index VDI that was an adaptation of a method described by Harris-Hooker (Harris-Hooker et al., *Neovascular Responses Induced by Cultured Aortic Endothelial Cells, J Cell. Phys.*, 114, 302-310, 1983). A plastic cover slip inscribed with 4, 5, 6, and 8 mm diameter concentric circles was centered over the adenosine pellet on the formalin-fixed CAM. The vascular density was judged by counting the numbers of the vessels which intersected the circles. This technique allowed counting of vessels down to 10-12 u in diameter. The positioning of the pellets on the CAM was randomized. From these experiments it can be seen that adenosine stimulated angiogenesis in the CAM model. The Elvax pellets themselves elicited no angiogenic responses. Adenosine was delivered by other means as well. Adenosine stimulated angiogenesis in the CAM assay.

Adenosine receptor subtype selective agonists stimulate angiogenesis to varying degrees in the CAM. In these studies, sterile filter paper disks were used to apply drug or vehicle to the CAM of eggs windowed after 7 days of incubation. The circular disk was 7 mm diameter. The agonist and antagonist drugs were delivered daily for 7 days in a volume of 100 μl placed onto the disks. On day 14 the CAMS were formalin fixed. The vessel density was determined by counting the vessels that intersected with the edge of the disks. Each bar represents data from between 13 and 19 eggs, with the exception of the bar for xanthine amine congener (XAC) which represents only four eggs. The results show a positive angiogenic response to the $A_1$ agonist CPA, the nonselective agonist NECA, and the $A_3$ selective ligand m-MECA. No angiogenic response was seen to the $A_{2A}$ agonist CGS21680 or other $A_{2A}$ selective agonists that were tried. The nonselective antagonist XAC did not inhibit baseline angiogenesis, in fact there may be slight stimulation. It is possible that some adenosine receptors may stimulate angiogenesis, while others, particularly the $A_{2A}$ receptor, may inhibit it. Hence, XAC may release some inhibition. The 100 nM doses used should have allowed some preservation of subtype selectivity for the ligands.

Fertile White Leghorn chicken eggs are obtained from Truslow Labs (Maryland) are these two companies? and incubated until day 7 post-fertilization at 37° C. The eggs were automatically rotated by the incubator. On day 7 the eggs were candled to check for viability. The eggshell surface was cleaned with betadine and 70% isopropanol. A window 1.5× 1.5 cm was cut into each egg over the CAM. The window was covered with clear cellophane tape and the eggs incubated at 37° C. overnight. The following day a sterile filter paper disc was applied to the CAM for the daily delivery of drugs or vehicle in a volume of 100 μl. CAMs were fixed on day 14 and vessels counted using the aforementioned method of Harris-Hooker et al.

The compound designated ATL-MC2015 is one of a new class of selective adenosine $A_1$ receptor allosteric enhancers.

ATL-MC2015 was assayed as described above for its efficacy in increasing vasculature in the CAM compared to those samples treated with vehicle alone. Vehicle consisted of 0.5% DMSO. Treatment was with 10 micromolar ATL-MC2015. Fifty microliter aliquots of vehicle (0.5% DMSO) or test compound (10 uM ATL-MC2015) were applied to the filter paper disc daily from day 7 to day 13. On day 14 the membranes were harvested and the vessels emerging at greater than 45 degrees from the disc were counted and compared between controls and treatment eggs. There were five eggs in the control group and three in the treatment group. There were an average of 75 vessels in control eggs and 94 in the treatment eggs.

Drug application into rat mesentery using infusion pumps. Alzet osmotic pumps were filled with drug or vehicle to a volume of 200 µl. The abdominal cavities of anesthetized 150 g Sprague-Dawley rats were incised and pumps implanted into the intraperitoneal cavity. The pumps delivered the drug at 1.0 µl/hr. After one week mesenteric samples were taken between vascular arcades along the length of the small bowel. Specimens were fixed and stained using a BS:lectin stain.

Angiogenesis stimulated by the $A_1$ agonist, CPA, was blocked by the A1-selective blocker WRC-0571.

CPA at 100 nM with or without 1 µM WRC-0571 was applied to filter paper discs on developing CAMS as described above. The angiogenic effect of the drug was completely blocked by the addition of the antagonist.

Allosteric enhancers of adenosine $A_1$ receptors stimulated angiogenesis. PD enhances the effects of endogenous adenosine on the chicken $A_1$ receptor in the CAM. PD at a concentration of 100 µM, or vehicle, was delivered to the CAM on a filter paper disc using a protocol identical to that used for adenosine agonists. The data show that PD stimulated angiogenesis by 10%. A small effect such as this in the absence of applied ligand or ischemia/hypoxia (which would increase the endogenous adenosine levels) is expected. Because it is a rapidly growing tissue, the CAM probably has higher levels of adenosine than more quiescent tissues, resulting in a measurable effect. The effects of PD were completely blocked by WRC-0571 which also blocked the effects of endogenous adenosine as well, suggesting its usefulness as an inhibitor of angiogenesis. The enhancer effect is a property of the family of compounds to which PD 81,723 belongs, not specific to PD 81,723 itself. C17, another allosteric enhancer, also stimulates angiogenesis and is blocked by WRC-0571.

There is synergism between agonist and PD 81,723. A concentration of 20 nM CPA did not stimulate angiogenesis in the CAM. The combination of low dose CPA with PD 81,723 resulted in stimulation of angiogenesis that was threefold greater than that seen with PD 81,723 alone. This experiment shows promise for using PD 81,723 to augment the effects of high tissue levels of adenosine.

Stimulation of angiogenesis by PD 81,723 is also seen in a mature mammalian animal model, via chronic infusion of PD 81,723 using Alzet pumps into the peritoneal cavity of a rat. The chronic infusion was an advantage because the model is not an ischemic one, so steady long term administration of the PD 81,723 may help to augment the effects of lower concentrations of endogenous adenosine.

This invention includes the 2-aminothiazole compounds described herein, pharmaceutical compositions for treatment of conditions and diseases in mammalian and human subjects which comprise a pharmaceutically acceptable carrier or diluent and such compound of the invention or a pharmaceutically acceptable salt thereof, novel intermediates, methods of preparing the inventive compounds and intermediates, and methods of using the inventive compounds in the treatment of conditions which may be treated by the promotion of angiogenesis.

When used in pharmaceutical preparations, the compounds of this invention may be useful in the form of the free base, in the form of salts and as a hydrate. All forms are within the scope of the invention. Acid addition salts may be formed and are simply a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the present invention can be administered to a mammalian subject in a variety of forms adapted to the chosen route of administration, i.e., orally, or parenterally. Parenteral administration is preferred, and in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations generally contain at least 0.1% of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be-coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Preferably, the active compound is administered parenterally or intraperitoneally. Solutions of the active compound as a free base or pharmacologically acceptable salt can be prepared in sterile water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the formulations must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammalian subject alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached.

The stimulation of new blood vessel growth to ischemic tissues, including the heart, brain, and extremities could dramatically impact morbidity and mortality from atherosclerotic diseases. The data show that adenosine $A_1$ receptors may play a role in the angiogenic response in addition to their other tissue protective properties and could potentially lead to new therapeutic strategies for the treatment of ischemia. The particular appeal with the allosteric enhancers is that they do not act alone, but would be most effective in hypoxic tissues with increased levels of endogenous adenosine. This could avoid some of the potential systemic adverse effects that may be seen with other therapies. There are also some advantages in choosing a secondary, rather than a primary, angiogenic factor that have already been discussed. Blockers of $A_1$ receptors are also promising for use to inhibit neovascularization where it causes or augments pathology, or as contraceptive agents to decrease the likelihood of implantation.

In accordance with one embodiment of the invention, a method for treating stroke, heart disease, and peripheral vascular disease is provided. The method comprises the step of administering to a patient a selective adenosine $A_1$ allosteric enhancer in an amount effective to induce angiogenesis at a desired location. The administered compositions can be localized in the desired tissues by any of the standard techniques known to those skilled in the art. These include direct application to the target area, either by topical application or by injection directly into or adjacent to the target tissues, or by general administration followed by targeting to the target tissue or selective accumulation to the target tissues. The compositions of the present invention can be targeted by linking the active agents to compounds that have a selective affinity for the target tissue. For example a compound of the invention can be linked to a monoclonal antibody that is specific for an antigen only present in the target tissue.

All publications, patents and patent documents cited herein are incorporated by reference as though individually incorporated by reference. The invention has been described with reference to various specific and preferred embodiments and techniques. However, it should be understood that many variations and modifications may be made by those skilled in the art while remaining within the spirit and scope of the invention. It will be understood that each of the elements described above, or two or more together, may also find a useful application in other types of applications differing from the type described above. This includes, for example, veterinary applications as well as the medical applications described herein.

Without further analysis, the foregoing will so fully reveal the gist of the present invention that others can, by applying current knowledge, readily adapt it for various applications without omitting features that, from the standpoint of prior art, fairly constitute essential characteristics of this invention.

We claim:

1. A compound of the formula (I):

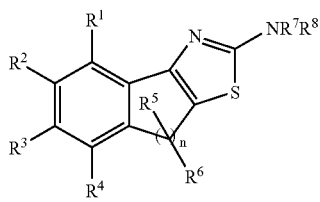

wherein n is an integer from 1 to 3;

$R^1$, $R^2$, $R^3$, and $R^4$ are each independently halo, alkyl, alkoxy, alkoxyalkyl, alkylamino, haloalkoxy, cycloalkyl, cycloalkoxy, cycloalkylamino, alkenyl, alkenoxy, alkenylamino, alkynyl, alkynoxy, alkynylamino, aryl, arylalkyl, heteroaryl, heteroarylalkyl, nitro, thio, alkylthio, alkylthioalkyl, alkylamide, alkylsulfoxy, alkylsulfonyl or ketoalkyl, with the aryl moiety in said aryl and arylalkyl groups, and the heteroaryl moiety in said heteroaryl and heteroarylalkyl groups, being optionally substituted with one or more substituents selected from halo, cyano, alkyl, aryl, heteroaryl, alkenyl, alkoxy, alkenyloxy, alkoxyalkyl, halosubstituted alkyl, halosubstituted alkoxy, alkoxycarbonyl, aminocarbonyl, nitro, thio, alkylthio, hydroxy, aryloxy, alkylamino, amino, alkylamide, arylamide, alkyihydroxy, acyloxy and alkylthioalkyl, and wherein $R^1$ and $R^2$, $R^2$ and $R^3$, or $R^3$ and $R^4$, together with the carbon atoms to which they are attached, may optionally form a 5, 6 or 7- membered ring containing zero to two heteroatoms selected from N, O and S and which may be optionally substituted with one or more substituents selected from halo, cyano, alkyl, alkenyl, alkoxy, alkenyloxy, alkoxyalkyl, halosubstituted alkyl, halosubstituted alkoxy, alkoxycarbonyl, aminocarbonyl, nitro, thio, alkylthio and alkylthioalkyl;

$R^5$ is hydrogen, halo or lower alkyl;

$R^6$ is independently selected from the group consisting of hydrogen, halo, alkyl, alkoxy, alkoxyalkyl, alkylamino, haloalkoxy, cycloalkyl, cycloalkoxy, cycloalkylamino, alkenyl, alkenoxy, alkenylamino, alkynyl, alkynoxy, alkynylamino, aryl, arylalkyl, heteroaryl, heteroarylalkyl, nitro, thio, alkylthio, alkylthioalkyl, alkylamide, alkylsulfoxy, alkylsulfonyl or ketoalkyl, with the aryl moiety in said aryl and arylalkyl groups, and the heteroaryl moiety in said heteroaryl and heteroarylalkyl groups, being optionally substituted with one or more substituents selected from halo, cyano, alkyl, aryl, heteroaryl, alkenyl, alkoxy, alkenyloxy, alkoxyalkyl, halosubstituted alkyl, halosubstituted alkoxy, alkoxycarbonyl, aminocarbonyl, nitro, thio, alkylthio, hydroxy, aryloxy, alkylamino, amino, alkylamide, arylamide, alkylhydroxy, acyloxy and alkylthioalkyl; and $R^7$ and $R^8$ are each independently hydrogen, alkyl or arylalkyl;

or a pharmaceutically acceptable salt thereof.

2. The compound of claim 1, wherein $R^5$, $R^6$, $R^7$ and $R^8$ are each hydrogen.

3. The compound of claim 2 wherein $R^1$, $R^2$, $R^3$ and $R^4$ are each independently hydrogen, halo, alkyl, alkoxy, alkoxyalkyl, alkylamino, haloalkoxy, cycloalkyl, cycloalkoxy, cycloalkylamino, and wherein $R^1$ and $R^2$, $R^2$ and $R^3$, or $R^4$, and $R^4$, together with the carbon atoms to which they are attached, form a 5, 6 or 7-membered ring which may optionally include one or two heteroatoms selected from N, O and S and which may be optionally substituted with one or more substituents selected from halo, cyano, alkyl, alkenyl, alkoxy, alkenyloxy, alkoxyalkyl, halosubstituted alkyl, halosubstituted alkoxy, alkoxycarbonyl, aminocarbonyl and alkylthio.

4. The compound of claim 1 wherein $R^1$, $R^2$, $R^3$ and $R^4$ is substituted or unsubstituted aryl or heteroaryl.

5. A method of treating ischemic disease in a mammal, including a human, by administering to said mammal an effective amount of a compound of claim 1, wherein the ischemic disease is selected from the group consisting of heart disease, stroke, and peripheral vascular disease.

6. A method of treating cardiac arrhythmias in a mammal, including a human, by administering to said mammal an effective amount of the compound of claim 1.

7. A method of treating chronic pain in a mammal, including a human, by administering to said mammal an effective amount of the compound of claim 1.

8. A method of inducing sleep in a mammal, including a human, by administering to said mammal an effective amount of the compound of claim 1.

9. A method of treating seizures in a mammal, including a human, by administering to said mammal an effective amount of the compound of claim 1.

* * * * *

UNITED STATES PATENT AND TRADEMARK OFFICE
CERTIFICATE OF CORRECTION

| | | |
|---|---|---|
| PATENT NO. | : 7,485,655 B2 | Page 1 of 1 |
| APPLICATION NO. | : 10/499291 | |
| DATED | : February 3, 2009 | |
| INVENTOR(S) | : Joel Linden et al. | |

It is certified that error appears in the above-identified patent and that said Letters Patent is hereby corrected as shown below:

IN THE SPECIFICATIONS:

Column 1, following line 10, please insert new section -- Statement of Government License Rights This invention was made through the support of the National Institutes of Health (Grant No. RO1 HL056111). The Federal Government has certain rights in this invention. --

Signed and Sealed this

Nineteenth Day of October, 2010

David J. Kappos
*Director of the United States Patent and Trademark Office*